US012662682B2

(12) United States Patent
Vesin-Auclair

(10) Patent No.: US 12,662,682 B2
(45) Date of Patent: Jun. 23, 2026

(54) METHOD FOR PRODUCING BIOLUMINESCENT PLANTS

(71) Applicant: WOODLIGHT, Illkirch-Graffenstaden (FR)

(72) Inventor: Rose-Marie Vesin-Auclair, Illkirch-Graffenstaden (FR)

(73) Assignee: WOODLIGHT, Illkirch-Graffenstaden (FR)

( * ) Notice: Subject to any disclaimer, the term of this patent is extended or adjusted under 35 U.S.C. 154(b) by 153 days.

(21) Appl. No.: 17/791,253

(22) PCT Filed: Jan. 6, 2021

(86) PCT No.: PCT/EP2021/050103
§ 371 (c)(1),
(2) Date: Jul. 7, 2022

(87) PCT Pub. No.: WO2021/140108
PCT Pub. Date: Jul. 15, 2021

(65) Prior Publication Data
US 2023/0416768 A1 Dec. 28, 2023

(30) Foreign Application Priority Data
Jan. 7, 2020 (FR) ................................. FR2000104

(51) Int. Cl.
*C12N 15/82* (2006.01)
(52) U.S. Cl.
CPC ..... *C12N 15/8214* (2013.01); *C12N 15/8243* (2013.01)
(58) Field of Classification Search
None
See application file for complete search history.

(56) References Cited

U.S. PATENT DOCUMENTS

| | | | | |
|---|---|---|---|---|
| 5,877,402 | A * | 3/1999 | Maliga | C12N 15/8214 536/23.6 |
| 6,297,054 | B1 * | 10/2001 | Maliga | C12N 15/8214 435/468 |
| 6,492,578 | B1 * | 12/2002 | Staub | C12N 15/8214 536/23.6 |
| 6,512,162 | B2 * | 1/2003 | McBride | C12N 15/8214 536/23.6 |
| 7,129,391 | B1 * | 10/2006 | Daniell | C12N 15/8214 435/320.1 |
| 2009/0220536 | A1 * | 9/2009 | Ofek | C07K 14/005 424/188.1 |
| 2009/0246227 | A1 * | 10/2009 | Friedman | C12N 7/00 424/231.1 |
| 2009/0263403 | A1 * | 10/2009 | Bakker | A61P 37/00 435/375 |
| 2013/0074221 | A1 * | 3/2013 | Krichevsky | C12N 15/8242 435/320.1 |
| 2021/0115476 | A1 | 4/2021 | Yampol'skiy | |
| 2022/0267784 | A1 | 8/2022 | Sorokin et al. | |

FOREIGN PATENT DOCUMENTS

| | | |
|---|---|---|
| WO | 2009017821 A1 | 2/2009 |
| WO | 2020005120 A1 | 1/2020 |

OTHER PUBLICATIONS

Daniell et al., Genome biology 17 (2016): 1-29 (Year: 2016).*
"Orchid", Wikipedia; https://en.wikipedia.org/wiki/Orchid; Last updated: Feb. 15, 2024 (Year: 2024).*
Wang, et al., Trends in plant science (2024): 1-16; DOI: 10.1016/j.tplants.2023.12.014 (Year: 2024).*
Mitiouchkina, et al., BioRxiv (2019): 809376.; Published Oct. 18, 2019 (Year: 2019).*
Díaz et al., Chloroplast Biotechnology: Methods and Protocols (2014): 165-175. (Year: 2014).*
Bock. Annual Review of Plant Biology 66 (2015): 211-241 (Year: 2015).*
GenBank Accession KU199713.1 (Year: 2016) https://www.ncbi.nlm.nih.gov/nuccore/KU199713.1; available Mar. 5, 2016.*
GenBank Accession KY930503.1 (Year: 2018) https://www.ncbi.nlm.nih.gov/nuccore/KY930503.1/; available: Apr. 1, 2018.*
Jakubiec et al, 2021, Nature Plants 7:932-941.*
Maliga, 2022, Nature Plants 8:996-1006.*
Kotlobay et al (2018, PNAS 115:12728-12732).*
Davarpanah et al (2009, J. Plant Biol. 52:244-250).*
Tabatabaei et al, 2019, Plant Biotechnol. J. 17:638-649.*
International Search Report and Written Opinion issued on Mar. 12, 2021 for corresponding PCT Application No. PCT/EP2021/050103.
Alexey A. Kotlobay et al., "Genetically encodable bioluminescent system from fungi," Proceedings of the National Academy of Sciences, US, vol. 115, No. 50, 2018, pp. 12728-12732 XP055689712.
Tatiana Mitiouchkina et al., "Plants with self-sustained luminescence," bioRxiv, 2019, pp. 1-17 XP055689716.
Alexander Krichevsky et al., "Autoluminescent Plants," PLOS One, vol. 5, No. 11, 2010, pp. el15461 XP055300217.
Delphine Prod'homme et al.; "Targeting of the Turnip Yellow Mosaic Virus 66K Replication Protein to the Chloroplast Envelope Is Mediated by the 140K Protein," Journal of Virology, vol. 77, No. 17, 2003, pp. 9124-9135.
Anna Jakubiec et al.; "Assembly of Turnip Yellow Mosaic Virus Replication Complexes: Interaction between the Proteinase and Polymerase Domains of the Replication Proteins," Journal of Virology, vol. 78, No. 15, 2004, pp. 7945-7957.

(Continued)

*Primary Examiner* — Anne Kubelik
(74) *Attorney, Agent, or Firm* — Maier & Maier, PLLC

(57) ABSTRACT

The present invention concerns bioluminescent plants and methods for producing them. Among said methods, the invention relates, in particular, to a method of introducing luciferase genes and luciferin biosynthesis genes into the chloroplasts of a plant. In addition, the invention concerns a method of producing light comprising adding chemical compounds to a culture medium of the plant according to the invention.

10 Claims, No Drawings

Specification includes a Sequence Listing.

(56)　　　　　References Cited

OTHER PUBLICATIONS

Anna Jakubiec et al.; "Phosphorylation of Viral RNA-dependent RNA Polymerase and Its Role in Replication of a Plus-strand RNA Virus," The Journal of Biological Chemistry, vol. 281, No. 30, 2006, pp. 21236-21249.

Anna Jakubiec et al.; "Proteolytic Processing of Turnip Yellow Mosaic Virus Replication Proteins and Functional Impact on Infectivity," Journal of Virology, vol. 81, No. 20, 2007, pp. 11402-11412.

Anna Jakubiec et al.; "Regulation of positive-strand RNA virus replication: The emerging role of phosphorylation," Virus Research, vol. 129, 2007, pp. 73-79.

Laurent Camborde et al.; "The Ubiquitin-Proteasome System Regulates the Accumulation of Turnip yellow mosaic virus RNA-Dependent RNA Polymerase during Viral Infection," The Plant Cell, vol. 22, 2010, pp. 3142-3152.

Anna Jakubiec et al.; "*Arabidopsis* DRB4 protein in antiviral defense against Turnip yellow mosaic virus infection," The Plant Journal, vol. 69, 2012, pp. 14-25.

Joris Beld et al.; "The Phosphopantetheinyl Transferases: Catalysis of a Posttranslational Modification Crucial for Life," Nat. Prod. Rep., vol. 31, No. 1, 2014, pp. 61-108.

Georg Hölzl et al.; "Chloroplast Lipids and Their Biosynthesis," Annual Reviews, Annual Review of Plant Biology, vol. 70, 2019, pp. 51-81.

Armando Alcázar Magaña et al.; "Caffeoylquinic acids: chemistry, biosynthesis, occurrence, analytical challenges, and bioactivity," Plant Journal, vol. 107, No. 5, 2021, pp. 1299-1319.

R. L. Airth et al.; "Enzymes Associated With Bioluminescence in Panus Stypticus Luminescens and Panus Stypticus Non-Luminescens," Journal of Bacteriology, vol. 88, No. 5, 1964, pp. 1372-1379.

Anderson G. Oliveira et al.; "The enzymatic nature of fungal bioluminescence," Photochemical & Photobiological Sciences, vol. 8, No. 10, 2009, pp. 1349-1488.

R. L. Airth et al.; "The Isolation of Catalytic Components Required for Cell-free Fungal Bioluminescence," Archives of Biochemistry and Biophysics, vol. 97, 1962, pp. 567-573.

A. Yu. Gorokhovatsky et al.; "The Recombinant Luciferase of the Fungus *Neonothopanus nambi*: Obtaining and Properties," Biochemistry, Biophysics and Molecular Biology, vol. 496, 2021, pp. 52-55.

Imbi Kurvet et al.; "LuxCDABE—Transformed Constitutively Bioluminescent *Escherichia coli* for Toxicity Screening Comparison with Naturally Luminous Vibrio fischeri," Sensors, vol. 11, 2011, pp. 7865-7878.

Alexey A. Kotlobay et al.; "Genetically encodable bioluminescent system from fungi," PNAS, vol. 115, No. 50, 2018, pp. 12728-12732.

Anna Hennig et al.; "Expression of the recombinant bacterial outer surface protein A in tobacco chloroplasts leads to thylakoid localization and loss of photosynthesis," FEBS Journal, vol. 274, 2007, pp. 5749-5758.

Ralph Bock; "Engineering Plastid Genomes: Methods, Tools, and Applications in Basic Research and Biotechnology," Plastid Genetic Engineering, Annu. Rev. Plant Biol., vol. 66, 2015, pp. 211-241.

Niaz Ahmad et al.; "Investigating the Production of Foreign Membrane Proteins in Tobacco Chloroplasts: Expression of an Algal Plastid Terminal Oxidase," PLOS One, vol. 7, issue 7, 2012, pp. e41722.

Kwang-Chul Kwon et al.; "Expression and assembly of largest foreign protein in chloroplasts: oral delivery of human FVIII made in lettuce chloroplasts robustly suppresses inhibitor formation in haemophilia A mice," Plant Biotechnology Journal, vol. 16, 2018, pp. 1148-1160.

Arjun Khakhar et al.; "Building customizable auto-luminescent luciferase-based reporters in plants," Plant Biology, eLife, vol. 9, 2020, pp. e52786; 1-18.

Peng Zheng et al.; "Metabolic engineering and mechanical investigation of enhanced plant autoluminescence," Plant Biotechnology Journal, vol. 21, 2023, pp. 1671-1681.

Xiuli Shen et al.; "Recent Advances in the Application of Plant Tissue Culture of Dieffenbachia," International Journal of Plant Developmental Biology, vol. 2, No. 2, 2008, pp. 82-91.

Xiuli Shen et al.; "Indirect shoot organogenesis from leaves of *Dieffenbachia* cv. Camouflage," Plant Cell Tiss. Organ. Cult., vol. 89, 2007, pp. 83-90.

Mohamed El-Sayed El-Mahrouk et al.; "Indirect shoot organogenesis and plantlets regeneration from stem of ornamental *Dieffenbachia maculata* cv. Marianna," Acta Biologica Szegediensis, vol. 51, No. 2, 2007, pp. 113-116.

Mahsa Rashidi et al.; "Effect of plant growth regulators on Fittonia verschaffeltii regeneration at in vitro conditions," Journal of Plant Physiology and Breeding, vol. 8, No. 2, 2018, pp. 59-68.

Marianne S. Banks et al.; "Callus and Shoot Formation in Organ and Tissue Cultures of *Hedera helix* L., English Ivy," Planta, vol. 145, 1979, pp. 205-207.

Y. E. Choi et al.; "Production of herbicide-resistant transgenic Panax ginseng through the introduction of the phosphinothricin acetyl transferase gene and successful soil transfer," Plant. Cell. Rep., vol. 21, 2003, pp. 563-568.

Krystyna Klimaszewska, "Plant regeneration from petiole segments of some species in tissue culture," Acta Agrobotanica, vol. 34, No. 1, 1981, pp. 5-28.

J.R. Liu et al.; "XIII Genetic Transformation of *Panax ginseng* (Ginseng)," Biotechnology in Agriculture and Forestry, vol. 45, 1999, pp. 193-194.

Vito S. Polito et al.; "Growth of Calluses Derived From Shoot Apical Meristems of Adult and Juvenile English Ivy (*Hedera helix* L.)," Plant Science Letters, vol. 22, 1981, pp. 387-393.

B. D. Reynolds et al.; "Embryogenesis and Plantlet Regeneration from Callus of Hibiscus acetosella," J. Amer. Soc. Hort. Sci., vol. 108, No. 2, 1983, pp. 307-310.

M.M. Belarmino et al.; "Agrobacterium-mediated genetic transformation of a phalaenopsis orchid," Plant Cell Reports, vol. 19, 2000, pp. 435-442.

Adelheid R. Kuehnle et al.; "Transformation of Dendrobium orchid using particle bombardment of protocorms," Plant Cell Reports, vol. 11, 1992, pp. 484-488.

Shu-Hong Lee et al.; "Establishment of an Agrobacterium-mediated genetic transformation procedure for the experimental model orchid *Erycina pusilla*," Plant Cell Tiss Organ Cult, vol. 120, 2015, pp. 211-220.

S. Men et al.; "Genetic transformation of two species of orchid by biolistic bombardment," Plant Cell Rep, vol. 21, 2003, pp. 592-598.

E. Semiarti et al.; "Establishment of High-frequency Genetic Transformation Method of Indonesian Orchid Species Mediated by Agrobacterium tumefaciens," Proceedings of Nioc 2011, Nagoya, Japan, pp. 32-39.

Jaime A. Teixeira da Silva et al.; "Somatic Embryogenesis in Two Orchid Genera (*Cymbidium, Dendrobium*)," Methods in Molecular Biology, vol. 1359, 2016, pp. 371-386.

J. Yang et al.; "Genetic transformation of Cymbidium orchid by particle bombardment," Plant Cell Reports, vol. 18, 1999, pp. 978-984.

Mikhajlo K. Zubko et al.; "Stable transformation of petunia plastids," Transgenic Research, vol. 13, 2004, pp. 523-530.

Pradeep K. Agarwal et al.; "Regeneration of Plantlets From Leaf and Petiole Explants of Pelargonium X Hortorum," In Vitro Cell. Dev. Biol.—Plant, vol. 36, 2000, pp. 392-397.

Anber Hassanein et al.; "Highly efficient transformation of zonal (Pelargonium x hortorum) and scented (P. capitatum) geraniums via Agrobacterium tumefaciens using leaf discs," Plant Science, vol. 169, 2005, pp. 532-541.

Margaret J. Hutchinson et al.; "Role of purine metabolism in thidiazuron-induced somatic embryogenesis of geranium (Pelargonium x hortorum) hypocotyi cultures," Physiologia Plantarum, vol. 98, 1996, pp. 517-522.

R.M. Madakadze et al.; "Effect of growth regulators on maturation of geranium (Pelargonium X hortorum) somatic embryos," Plant Growth Regulation, vol. 30, 2000, pp. 55-60.

(56)                           References Cited

OTHER PUBLICATIONS

B. N. S. Murthy et al.; "Characterization of somatic embryogenesis in Pelargonium X hortorum mediated by a bacterium," Plant Cell Reports, vol. 18, 1999, pp. 607-613.

Jin Cui et al.; "Plant Regeneration through Protocorm-like Bodies Induced from Nodal Explants of Syngonium podophyllum 'White Butterfly'," Hortscience, vol. 43, No. 7, 2008, pp. 2129-2133.

Priya Khetarpal et al.; "In vitro regeneration in Syngonium 'Mini Pixie' via protocorm like bodies," International Journal of Pure & Applied Bioscience, vol. 3, No. 2, 2015, pp. 400-406.

X. Wang et al.; "In Vitro Culture of Epipremnum aureum, Syngonium podophyllum, and Lonicera macranthodes, Three Important Medicinal Plants," Acta Hort., vol. 756, 2007, pp. 155-162.

Qian Zhang et al.; "Regeneration of Syngonium podophyllum 'Variegatum' through direct somatic embryogenesis," Plant Cell, Tissue and Organ Culture, vol. 84, 2006, pp. 181-188.

* cited by examiner

METHOD FOR PRODUCING BIOLUMINESCENT PLANTS

CROSS-REFERENCE TO RELATED APPLICATIONS

This application is a national stage application (under 35 U.S.C. § 371) of PCT/EP2021/050103, filed Jan. 6, 2021, which claims benefit of French Application No. FR2000104, filed Jan. 7, 2020, which are incorporated herein by reference in their entireties.

The field of the invention is plant biology.

Bioluminescence is the production and emission of light by a living organism via a chemical reaction in which chemical energy is converted into light energy.

The basic substrate for luminescence is luciferin, which emits light by oxidation through the action of the enzyme luciferase. In bacteria, the expression of genes related to bioluminescence is controlled by the lux operon. Other organisms are also capable of bioluminescence, such as certain fungi or multicellular beings, including a large number of marine species.

There is a large number of natural luciferases found in species from very different environments. They are found in different families of insects such as the firefly (*Photinus pyralis*) or in a family of beetles, the click beetle, or in worms (*Phrixothrix hirtus*). Luciferases are also found in different marine species (*Renilla reniformis, Gaussia princeps, Cypridina hilgendorfii* . . . ) and in some bacteria (*Photobacterium phosphoreum* or *Vibrio harveyi*). This kind of mechanism is also found in some fungi (e.g. *Panellus stipticus*) or in phytoplankton (Haddock et al., Ann Rev Mar Sci. 2010; 2:443-93; Wilson and Hastings, Annu Rev Cell Dev Biol. 1998; 14:197-230).

The chemical structure of luciferin varies from species to species and can be referred to as coelenterazine. Identification of the metabolic pathway for coelenterazine or luciferin synthesis is important to enable the development of bioluminescent systems to which luciferin need not be added to achieve the bioluminescent effect.

Kotlobay et al (Proc Natl Acad Sci USA. 2018 Dec. 11; 115 (50): 12728-12732) described mechanisms of luciferin formation and recycling in fungi and identified three enzymes in addition to luciferase (Luz). Hispidine synthase (HispS) converts caffeic acid to hispidine, which in turn is a substrate for the enzyme hispidine-3-hydroxylase (H3H), which converts hispidine to luciferin (3-hydroxyhispidine). Finally, caffeylpyruvate hydrolase (CPH) converts oxyluciferin (caffeoyl-pyruvic acid), obtained after oxidation of luciferin by luciferase, to caffeic acid. However, the authors did not describe that this system can be used in plants in general and chloroplasts in particular.

Mitiushkina et al (BioRxiv, 2019, doi.org/10.1101/809376) described that expression of the *Neonothopanus nambi* HispS, H3H, and Luz genes in tobacco cells (integration into the nuclear genome) generated luminescent plants. The authors did not use the NpgA gene.

The teaching of WO2020005120A1 is similar to that of the above two documents.

Krichevsky et al (PLOS ONE 5 (11): e15461) describe self-luminescent plants using the lux operon of *Photobacterium leiognathi* (luxCDABEG) to transform chloroplasts. The different transgenes used (spectinomycin and streptomycin antibiotic resistance gene (aadA) and lux operon (luxCDABEG)) are under the control of the same chloroplast promoter. Thus, 7 genes were introduced as an operon under the control of a single chloroplast promoter. WO2009017821 shows the same teaching as the previous document.

Bioluminescent plants can be used in the field of decoration and events. Preferably, such plants should be able to produce light autonomously, or after providing a low cost substrate. The amount of light that needs to be produced should be sufficient for the effect to be aesthetically pleasing. It is also preferred that these plants are sterile to avoid any contamination in the environment.

In order to address the above issues, the Applicant has developed a plant in which at least one chloroplast of a cell contains the genes encoding the proteins hispidin-3-hydroxylase (H3H, GenBank: BBH43497.1) and luciferase (Luz, GenBank: BBH43509.1) under the control of promoters active in the chloroplast. Thus, the chloroplast contains an expression cassette for the H3H and Luz proteins in chloroplasts.

In one particular embodiment, a plurality of chloroplasts of the cell contains the expression cassette. In another embodiment, a plurality of cells of the plant contains at least one chloroplast containing the expression cassette. In a particular embodiment, all cells of the plant contain at least one chloroplast containing the expression cassette. In this embodiment, at least 50% of the chloroplasts of the plant contain the expression cassette, i.e., if one takes a portion of the plant and investigates the presence of the expression cassette in the chloroplasts of that portion of the plant, at least 50% contain that cassette. This can be easily verified by any method known in the art such as quantitative PCR, the preferred method.

It is interesting to process plant chloroplasts (or plastids) for several reasons:

- these are present in large quantities in each cell, which allows to multiply the quantity of enzymatic reaction points producing bioluminescence
- the chloroplasts are present in the cytoplasm of the cell and are not transmissible by pollen, which avoids contamination to other plants of the same species
- there are several copies of the genome in each chloroplast, which also allows to multiply the amount of enzymatic reaction points producing bioluminescence.

Transformation of Chloroplasts

Although methods for plastid transformation are known in the art, chloroplast transformation is, in general, much more complicated, time consuming and with a much lower success rate than nuclear transformations. This is especially true when large or multiple genes are to be integrated.

Chloroplasts can be transformed by biolistics. The meristematic tissues (cells) are bombarded with gold microbeads coated with DNA. After divisions, the number of transformed plastids will increase more rapidly than the non-transformed plastids (especially when using a selection medium), and the non-transformed plastids will be "lost" by dilution.

Alternatively, the PEG (polyethylene glycols) method can be used. The destabilization of plasma membranes in the presence of PEGs allows the entry of transgenes into chloroplasts.

Transgenes

The invention thus relates to a plant in which at least one chloroplast of a cell contains genes encoding the proteins hispidine-3-hydroxylase (H3H) and luciferase (Luz) under the control of promoters active in the chloroplast.

The invention also relates to a plant cell in which at least one chloroplast of a cell contains genes encoding the proteins hispidin-3-hydroxylase (H3H) and luciferase (Luz)

under the control of promoters active in the chloroplast. It is possible to regenerate a complete plant from this cell.

The cell so described can produce light by adding hispidin to the culture medium. When this cell is present in a plant, the hispidin present in the culture medium reaches the cell via the sap.

In the chloroplast, hispidin is then converted to luciferin by the enzyme H3H, and then luciferin is oxidized to oxyluciferin by luciferase Luz, producing light. This method allows luminescence to be obtained only when the substrate (hispidin) is supplied to the plant.

In another embodiment, the chloroplasts of plant cells contain, in addition to the genes encoding the H3H and Luz enzymes, a gene encoding the hispidin synthase enzyme HispS, under the control of a promoter active in the chloroplasts. In this embodiment, luminescence will be initiated by caffeic acid naturally present in the plant cell (cytoplasm) and in the chloroplast. It is then transformed into hispidin, which then gives luciferin. Alternatively, luminescence can be initiated by adding caffeic acid to the culture medium.

In this embodiment, the cell can thus produce luminescence in an autonomous way, i.e. it contains all the genes allowing the synthesis of luciferin, as well as its recycling.

In another embodiment, however, it is preferred that it contains all the genes for the synthesis of luciferin, as well as the genes for the recycling of caffeoyl-pyruvic acid, the reaction product of luciferase on luciferin, in order to avoid its accumulation and a risk of caffeic acid deficiency.

In this embodiment, the chloroplast contains genes encoding the proteins caffeoyl pyruvate hydrolase (CPH, GenBank: BBH43519.1), hispidin synthase (HispS, GenBank: BBH43485.1), under the control of promoters active in the chloroplasts.

In a particular embodiment, the luciferase sequence is SEQ ID NO: 20 (with or without the poly_histidine tag, His-tag).

In a particular embodiment, the sequence of the H3H enzyme is SEQ ID NO: 21 (with or without the poly_histidine tag, His-tag).

In a particular embodiment, the sequence of the CPH enzyme is SEQ ID NO: 22 (with or without the poly_histidine tag, His-tag).

In a particular embodiment, the sequence of the HispS enzyme is SEQ ID NO: 23 (with or without the poly_histidine tag, His-tag).

In one embodiment, the chloroplast also contains a gene encoding a phosphopantetheinyl transferase (NpgA, NCBI Reference Sequence: XP_663744.1), also under the control of a promoter active in plastids. The gene encoding NpgA can be added for each embodiment as described above.

In a particular embodiment, the sequence of NpgA is SEQ ID NO: 24 (with or without the poly_histidine tag, His-tag).

In a particular embodiment, the plant is such that all of its cells contain at least one chloroplast (and preferably at least 50% of its chloroplasts) transformed by the genes encoding H3H, Luz, CPH, HispS and NpgA proteins.

The invention also relates to a plant cell in which at least 50% of the chloroplasts are transformed by the genes encoding the H3H, Luz, CPH, HispS and NpgA proteins.
Vectors The invention also relates to a vector containing
(a) an origin of replication in a bacterium or yeast, preferably an origin of replication in *Escherichia coli*,
(b) a nucleic acid sequence encoding the Luz protein (in particular SEQ ID NO: 1) under the control of a promoter functional in chloroplasts, (c) a nucleic acid sequence encoding the H3H protein (in particular SEQ ID NO: 2) under the control of a promoter functional in chloroplasts,
(d) two nucleic acid sequences present in a chloroplast, preferably trnI (SEQ ID NO: 6) and trnA (SEQ ID NO: 7), flanking said nucleic acid sequences (b) and (c), these sequences (b) and (c) being thus located between these two sequences (d).

In a particular embodiment, the vector also contains
(e) a nucleic acid sequence coding for a Cph protein (in particular SEQ ID NO: 3), located between sequences (d) with sequences (b) and (c).

In a particular embodiment, the vector also contains
(f) a nucleic acid sequence encoding a HispS protein (in particular SEQ ID NO: 4), located between sequences (d) with sequences (b) and (c).

In a particular embodiment, the vector also contains
(g) a nucleic acid sequence encoding an NpgA protein (in particular SEQ ID NO: 5), located between sequences (d) with sequences (b) and (c).

In a preferred embodiment, the vector contains the origin of replication (a), as well as the sequences (b), (c), (e), (f) and (g) flanked by the sequences (d).
Host Cells The invention also relates to a host cell containing a vector as described above. This cell is preferably a bacterial cell, preferably *Escherichia coli* transformed by the vector.
Optimization of Coding Sequences It is preferable that the nucleic sequence of the genes has been optimized for expression in chloroplasts (adaptation of chloroplast codon usages).

This can be based on the information given in Nakamura et al (Plant J. 2007 January; 49 (1): 128-34. 2006), Liu et al (J Genet. 2005 April; 84 (1): 55-62) or Zhang et al (Journal of Integrative Plant Biology 2007, 49 (2): 246-254). In particular, we use the databases of the Kazusa DNA Research Institute which can be found on their website https://www.kazusa.or.jp/codon.

The sequences SEQ ID NO: 1 to SEQ ID NO: 5 are thus sequences optimized for expression in chloroplasts. These sequences, or sequences having at least 90% identity, preferably at least 95% identity, more preferably at least 98% identity, most preferably at least 99% identity with these sequences and encoding the proteins SEQ ID NO: 20 to SEQ ID NO: 24 respectively, can be used.

Preferably, the genes are optimized to obtain a GC rate between 35% and 40%. The codons preferentially expressed in the chloroplasts are also chosen, taking into account the data of Liu et al.
Organization The system used is a system derived from fungi (fungus). In particular, it is preferred to use the enzyme system from a fungus selected from *Neonothopanus nambi, Neonothopanus gardneri*, or *Omphalotus olearius*.

Preferably, it is preferred when all of the enzymes used (HispS, H3H, Luz, and CPH) are from the same organism, preferably *Neonothopanus nambi*. The use of sequences from *Neonothopanus gardneri*, which are very similar to those from *Neonothopanus nambi*, is also considered. Alternatively, some sequences from *Neonothopanus nambi* and others from *Neonothopanus gardneri* may be used together.

It is recalled that the npgA (4'-phosphopantetheinyl transferase) gene originates from *Aspergillus nidulans*.
Promoters and Coding Sequences
Operon In a first embodiment, the different genes are expressed under the control of a single promoter, in the form of an operon, as is known in the art, for genes involved in the same metabolic pathway (cf Saxena et al, 2014 J Biosci. 2014 March; 39 (1): 33-41; Kumar et al, 2012 Metab Eng. 2012 January; 14 (1): 19-28).

In this embodiment, a promoter selected from the PatpI, Prrn, PrbcL or PpsbA promoters (in particular those described by the sequences SEQ ID NO: 8 to SEQ ID NO: 12) can be used.

However, this embodiment is not preferred.

Individual Sponsors

In another embodiment, each transgene introduced into the chloroplast of the plant is under the control of its own promoter (a promoter of its own, it being understood that the same promoter can be used for two genes, but that it is preferred when at least two transgenes are under the control of two different promoters). In this embodiment, the transgenes are therefore not expressed within an operon. This is a preferred embodiment. Indeed, the fact of assigning to each gene an optimal regulation system (promoters and terminators) that is specific to it, allows to increase the expression levels, as compared to the use of a system based on an operon. This mode of operation thus goes against the modes generally observed in the art, summarized in Boehm and Bock (Plant Physiol. 2019 March; 179 (3): 794-802), which refers to recent research for optimal expression of several proteins in chloroplasts. This paper shows that as soon as simultaneous expression of two or more proteins is desired, genes are arranged as an operon such as for the expression of: polyhydroxybutyrate (Bohmert-Tatarev et al., Plant Physiol. 2011 April; 155 (4): 1690-708), insect proteins (De Cosa et al., Nat Biotechnol. 2001 January; 19 (1): 71-4) 7, or carotenoids (Hasunuma et al., Plant J. 2008 September; 55 (5): 857-68), but also for the expression of entire metabolic pathways such as those of: vitamin E (Lu et al., Proc Natl Acad Sci USA. 2013 Feb. 19; 110 (8): E623-32), artemisinic acid (Saxena et al., J Biosci. 2014 March; 39 (1): 33-41, Fuentes et al, eLife. 2016; 5: e13664), mevalonate (Kumar et al., Metab Eng. 2012 January; 14 (1): 19-28, Saxena et al., op. cit.) and dhurrin (Gnanasekaran et al., J Exp Bot. 2016 April; 67 (8): 2495-506).

Furthermore, Boehm and Bock (op. cit.) also recall the latest advances in improving the efficiency of synthetic operons; by adding intercistronic expression elements (IEEs) (Zhou et al., Plant J. 2007 December; 52 (5): 961-972), or by stabilizing messenger RNAs with proteins that bind to them (PRRs), (Legen et al., Plant J. 2018 April; 94 (1): 8-21). Even more recently, they recall that Fuentes et al. (op. cit.) have shown that the complexity and number of accessible pathways have been extended by a trick that combines chloroplast transformation with nuclear transformation ("combinatorial supertransformation of transplastomic recipient lines (COSTREL)"). These authors classically transformed tobacco plant chloroplasts with the artemisinic acid metabolic pathway (as an operon) and the nucleus of these plants once transformed with five genes (CYB5, ADH1, ALDH1, DBR2, DXR). With this approach, the authors improved the production of artemisinic acid by 77 times.

Thus, the art proposes rather to use operons and to optimize them (manufacture of synthetic operons), when one wishes to express several genes in chloroplasts, in particular when the genes considered must cooperate with each other in a given metabolic pathway.

In particular, the promoters PatpI, Prrn, PrbcL or PpsbA can be chosen.

Preferably, the H3h gene is under the control of the PpsbA promoter, in particular the portion specified in SEQ ID NO: 9.

Preferably, the Luz gene is under the control of the PpsbA promoter, in particular the portion specified in SEQ ID NO: 9.

Preferably, the Cph gene is under the control of the PrbcL promoter, in particular the portion specified in SEQ ID NO: 10.

Preferably, the HispS gene is under the control of the Prrn promoter, in particular the portion specified in SEQ ID NO: 11.

Preferably the npgA gene is under the control of the PatpI promoter, in particular the portion specified in SEQ ID NO: 12.

In one particular embodiment, sequences, and in particular promoters, are optimized by selecting particular 5'UTR sequences to optimize gene expression in chloroplasts (De Costa et al. Genes Genet Syst. 2001 December; 76 (6): 363-71); Drechsel and Bock Nucleic Acids Res. 2011 March; 39 (4): 1427-38); Shinozaki and Sugiura Gene. 1982 Nov. 20(1) 91-102 and Nucleic Acids Res. 1982 Aug. 25; 10(16): 4923-34; Kuroda and Maliga, Plant Physiol. 2001 January; 125 (1): 430-6).

Sequences SEQ ID NO: 9 to SEQ ID NO: 12 represent such optimized promoters with added 5'UTRs to enhance expression.

Thus, preferably, the H3h gene is under the control of the optimized promoter described by SEQ ID NO: 9.

Preferably, the Luz gene is under the control of the optimized PpsbA promoter described by SEQ ID NO: 9.

Preferably, the Cph gene is under the control of the optimized PrbcL promoter described in SEQ ID NO: 10.

Preferably, the HispS gene is under the control of the optimized Prrn promoter described in SEQ ID NO: 11.

Preferably the npgA gene is under the control of the optimized PatpI promoter described by SEQ ID NO: 12.

Terminators positioned 3' to the coding nucleic sequences are also used. The terminators represented by the sequences SEQ ID NO: 13 to SEQ ID NO: 18 can be used.

In a preferred embodiment, a (5'-3') SEQ ID NO: 9-SEQ ID NO: 1-SEQ ID NO: 14 construct is used to express Luz.

In a preferred embodiment, a (5'-3') SEQ ID NO: 9-SEQ ID NO: 2-SEQ ID NO: 15 construct is used to express H3H.

In a preferred embodiment, a (5'-3') SEQ ID NO: 10-SEQ ID NO: 3-SEQ ID NO: 16 construct is used to express Cph.

In a preferred embodiment, a (5'-3') SEQ ID NO: 11-SEQ ID NO: 4-SEQ ID NO: 14 construct is used to express HispS.

In a preferred embodiment, a (5'-3') SEQ ID NO: 12-SEQ ID NO: 5-SEQ ID NO: 18 construct is used to express NpgA.

In a preferred embodiment, a (5'-3') SEQ ID NO: 8-SEQ ID NO: 19-SEQ ID NO: 17 construct is used to express the aadA selection gene.

Integration of the Expression Cassette within the Chloroplasts

As seen above, in a particular embodiment, all the genes present in the chloroplasts form an expression cassette, i.e. these genes are present one after the other on a DNA fragment. Thus, the chloroplasts are transformed with this expression cassette, in order to obtain the expression of the genes coded in this expression cassette.

It is preferred when the genes are integrated into the chloroplast genome. In particular, homologous recombination is used to introduce the genes at a selected location in the chloroplast genome.

Many insertion sites are possible in the chloroplast genome. The preferred choice is to integrate the expression cassette in a non-coding region of the chloroplast genome. Once can use inter-gene sequences between two chloroplast transfer RNA coding sequences.

In particular, the trnI (SEQ ID NO: 6) and trnA (SEQ ID NO: 7) sites, coding for the isoleucine and alanine transfer RNAs, are chosen. One can use sequences SEQ ID NO: 6 or SEQ ID NO: 7, or sequences containing these sequences. Sequences included in SEQ ID NO: 6 or SEQ ID NO: 7 can also be used, but in this case, it is preferable to use sequences with at least 1000 bases, preferably at least 1300 bases, preferably at least 1500 bases, preferably at least 1700 bases of SEQ ID NO: 6 or SEQ ID NO: 7. In fact, in order to increase the chances of homologous recombination, it is preferable to use sequences that are as long as possible.

The sequences SEQ ID NO: 6 and SEQ ID NO: 7 are from tobacco (*Nicotiana benthamiana*). They are therefore particularly suitable for integration by homologous recombination in tobacco chloroplasts. However, they can be used for other plants, because of the high homology between these sequences and the trnI and trnA sequences of chloroplasts of other plants. Thus, sequences having at least 99% identity, more preferably at least 99.45% identity, more preferably at least 99.5% identity, more preferably at least 99.7% identity with SEQ ID NO: 6 or SEQ ID NO: 7 can be used.

Sequence Comparison/Determination of Percentage Identity

In order to evaluate the identity between two nucleic sequences, the Blastn® (nucleotide blast) software developed from Altschul et al, (1997), Nucleic Acids Res. 25:3389-3402; Altschul et al, (2005) FEBS J. 272:5101-5109, available on the NCBI website (https://blast.ncbi.nlm-.nih.gov/Blast.cgi) is used using the following parameters, given in English:

Max target sequences: 100
Select the maximum number of aligned sequences to display
Short queries: Automatically adjust parameters for short input sequences
Expect threshold: 10
Word size: 28
Max matches in a query range: 0
Scoring Parameters
Match/Mismatch Scores: 1,-2
Gap Costs: Linear
Filters and Masking
Filter: Low complexity regions filter: on
Mask : Mask for lookup table only : on In order to evaluate the identity between two protein sequences, the Blastp® (protein blast) software developed from Altschul et al, (1997), Nucleic Acids Res. 25:3389-3402; Altschul et al, (2005) FEBS J. 272:5101-5109, available on the NCBI website (https://blast.ncbi.nlm.nih.gov/Blast.cgi) is used using the following parameters, given in English:

Expected threshold : 10
Word size : 3
Max matches in a query range: 0
Matrix: BLOSUM62
Gap Costs: Existence 11, Extension 1.
Compositional adjustments: Conditional compositional score matrix adjustment
No filter for low complexity regions Plant The plant according to the invention is preferably an ornamental plant. It is preferably chosen from the group consisting of *Hedera helix, Petunia axillaris* subsp. *axillaris, Nicotiana benthamiana, Ficus benjamina, ficus elastica, Ficus microcarpa, Chlorophytum comosum, Monstera deliciosa, Sansevieria socotrana, Pelargoniumxhortorum, Spathiphyllum wallisii, Dracaena draco, Dracaena angustifolia, Yucca aloifolia, Beaucarnea recurvata, Syngonium podophyllum, Fittonia verschaffeltii, Aloe vera, Aloe jucunda, Aloe juvenna, Dieffenbachia. Livistona speciosa,* Orchidaceae. In particular, the plant is *Nicotiana benthamiana*. In another embodiment, the plant is *Petunia (Petunia axillaris* subsp. *Axillaris)*. In another embodiment, the plant is ivy (*Hedera helix*).

Production Method

The invention also relates to a method of producing a plant as described above, comprising a step of inserting the transgenes as described above into the genome of chloroplasts of plant cells. The method also preferably includes the step of regenerating a plant by callus culture.

In a first embodiment, the method comprises inserting transgenes encoding the H3H and Luz enzymes into the genome of plant cell chloroplasts.

In another embodiment, the method comprises inserting transgenes encoding Cph, H3H and Luz enzymes into the genome of plant cell chloroplasts.

In another embodiment, the method comprises inserting transgenes encoding the enzymes Cph, HispS, H3H and Luz into the genome of chloroplasts of plant cells.

In another embodiment, the method comprises inserting transgenes encoding the enzymes Cph, HispS, H3H and Luz into the genome of plant cell chloroplasts, as well as a transgene encoding NpgA.

In one embodiment, the integration of transgenes is performed by bombarding plant leaves with a plasmid using a particle gun. To do this, the expression cassette (DNA fragment carrying the transgenes that one wishes to integrate into the chloroplast genome) is prepared, and metal microbeads (preferably gold, but can also be tungsten) are coated, which are then projected onto the plant cells.

In another embodiment, the plant cells are contacted with polyethylene glycol (PEG), which destabilizes the plasma membranes and allows the entry of DNA fragments carrying the transgenes to be integrated into the plastid genome.

It is preferred when the integration of transgenes into the chloroplast genome is performed by homologous recombination. Thus, transgenes are flanked by sequences homologous to sequences of the chloroplast chromosome. The integration of the transgenes is thus performed by the organelle machinery by homologous recombination at the site In both cases, the transformed cells are cultivated under conditions that produce calluses, which are grown and from which a plant is regenerated by methods known in the art.

In a preferred embodiment, the callus culture is performed on a selective medium. A selective medium is a medium containing a selective element (often an antibiotic or herbicide) on which only cells containing a gene for resistance to the selective element can grow, while cells not containing the gene cannot grow or grow at a slower rate.

Selective elements include antibiotics: neomycin/kanamycin and nptII (aminoglycoside 3'-phosphotransferase), betain and badh (betain aldehyde dehydrogenase), hygromycin B and hpt (hygromycin B phosphotransferase), spectinomycin/streptomycin and aadA (aminoglycoside 3'-adenyltransferase), chloramphenicol and cat (chloramphenicol acetyltransferase), amikacin and aphA6 (3'-aminoglycoside phosphotransferase) sulfonamides and sull (dihydropteorate synthase DHPS), gentamycin and aacC1 (gentamycin acetyltransferase) or the herbicides bialophos/phosphinotricin/glufosinate and pat (phosphinotricin actyltransferase) glyphosate and gox (glyphosate oxidoreductase) or epsp (5 eonylpyruvyl shikimate-3-phosphate synthase), bromoxynil and bxn (bromosynil nitrilase), sulfonylureas/imidazolines/ triazolopyrimidines/pyrimidylbenzoates and als (acetolactate synthase).

In particular, the aadA (aminoglycoside 3'-adenyltransferase) gene that confers resistance to spectinomycin is used, a coding sequence of which is represented by SEQ ID NO: 19.

The resistance gene is introduced into the expression cassette containing the transgenes of interest, under the control of a promoter active in chloroplasts. Alternatively, a system can be implemented in which the resistance gene can be excised after transformation, e.g. following the teaching of Scutt et al (Biochemistry 84 (2002) 1119-1126) or Lantham et al (Nature Biotechnology, 2000, (18), 1172-76).

The invention also relates to a light system comprising a bioluminescence-emitting plant as described above, i.e., at least one cell of which contains at least one chloroplast containing the above-mentioned genes, and which emits bioluminescence by oxidation of luciferin by the enzyme Luz.

Preferably, the system contains a plant in which at least 50% of the chloroplasts contain the above-mentioned enzyme system.

The invention also relates to a method of producing light, comprising the step of adding hispidine to the culture medium of a plant as described above, and at least one chloroplast of which contains at least the genes encoding the H3H and Luz enzymes (preferably integrated into its genome).

The invention also relates to a method of producing light (by a plant), comprising the step of adding caffeic acid to the culture medium of a plant as described above, and at least one chloroplast of which contains at least the genes encoding the HispS, H3H and Luz enzymes (preferably integrated into its genome).

The invention also relates to a method of producing light (by a plant), comprising the step of adding caffeic acid to the culture medium of a plant as described above, and of which at least one chloroplast contains the genes encoding the HispS, H3H, Luz, Cph enzymes (preferably integrated in its genome).

Preferably the chloroplast also contains the gene encoding NpgA, in the above methods.

EXAMPLES

The following examples and figures describe a particular embodiment of the invention.

Example 1. Preparation of the Plasmid Containing the H3H and Luz Genes and the Sequences Allowing the Integration of these Genes into the Chloroplast Genome and their Expression The H3H and Luz gene sequences were adapted with chloroplast usage codons and then synthesized (SEQ ID NO: 2 and SEQ ID NO: 1). The promoters were selected from the set of promoters present in the chloroplast genome and modified in their 5'UTR sequence so as to maximize the expression of genes under their controls. These modified promoters were then synthesized. The terminators were selected from the set of terminators present in the chloroplast genome and some were optimized to be as short as possible while keeping their functions. They were also synthesized. The trnI and trnA sequences (SEQ ID NO: 6 and SEQ ID NO: 7) were chosen to allow the integration of the H3H and Luz genes in the chloroplast genome. They were amplified by PCR (Polymerase Chain Reaction) from chloroplast DNA of Nicotiana benthamiana. The spectinomycin/streptomycin resistance gene named aadA was amplified by PCR from a plasmid containing it (SEQ ID NO: 19).

To elaborate the plasmid vector containing all these sequences, the plasmid pUC19 was used. The promoters, genes and terminators were amplified by PCR and each part of the trio was ligated together: promoter, gene and terminator with the In-fusion® method from Takara. 50 ng or 100 ng of DNA was incubated at 50° C. for 1 h with the ligation enzymes from the In-fusion kit. The ligation products were then amplified by PCR.

The three genes (aadA, H3H, and Luz) thus fused with their respective promoters and terminators, and the trnI and trnA sequences were then cloned into the linearized pUC19 plasmid by PCR, following the NEBuilder® protocol.

The NEBuilder® is based on the "Gibson assembly" cloning strategy. The primers were designed so that the fragments have a 25 bp sequence overlap with each other and with the sequence of the pUC19 plasmid insertion site.

Gibson Reaction and Bacterial Transformation 1. 40 to 75 ng of DNA from each PCR product is used with NEBuilder® HiFi DNA assembly 2× buffer and incubated for 1 h at 50° C. 2. 10-alpha NEB competent bacteria are transformed with the ligation products by heat shock, incubated for 1 h at 37° C. and then plated on LB agar plate with antibiotic and incubated overnight at 37° C. 3. Plasmid DNA from about 15 clones is extracted and analyzed by sequencing. 4. The positive clones are then amplified in a larger volume of LB+antibiotic (100 ml) and their plasmid DNA is extracted and analyzed by sequencing.

Transformation of Tobacco Plants with the Obtained Plasmids

Coating the Gold Beads with Plasmid DNA

Materials required: 1. 100% ethanol. 2. Sterile gold beads (Biorad®). 3. 2.5M CaCl2. 4. 0.1 M spermidine, 5. in vitro plant growth medium: MS with vitamins supplemented with 3% sucrose. 6. Hormones 6-benzyl aminopurine (BAP), indole-3-acetic acid (IAA), indole3-butyric acid (IBA), at the concentration of 1 mg/ml. 7. Spectinomycin at 500 mg/L.

The gold beads are prepared following the Biorad® protocol provided with the beads.

The plasmid DNA is then precipitated onto the gold beads (for 5 samples): 1. Vortex 50 µL of gold beads for 1 minute. 2. Add 10 µL of plasmid DNA (at 1 µg/µL) and vortex the mixture. 3. Add 50 µL of 2.5 M Cacl2 and vortex the mixture. 4. Add 20 µL of 0.1 M spermidine and vortex the mixture. The beads are then washed with 100% ethanol and resuspended in 40 µl of 100% ethanol Bombardment of Nicotiana benthamiana Leaves with Gold Beads Preparation of the bombardment chamber: 1. wash the chamber and the grids with 70% ethanol 2. Place the gold beads coated with plasmid DNA on the grid provided. 3. Place the intact sheet on Whatman® No. 1 filter paper placed on antibiotic-free medium. Place the sample and close the bombardment chamber. 4. Turn on the pump to reach the expected pressure and press the button to fire. 5. Stop the pump to release the pressure and open the chamber. 6. Incubate the bombarded samples on the box for 2 days in the dark. On the third day, cut the explants 3-5 mm square and place them on selection medium (MS supplemented with 3% sucrose and hormones: 1 mg/L BAP, and 0.1 mg/IAA, with 500 mg/L spectinomycin. 3. Transgenic stems appear after 3 to 5 weeks of transformation. Cut the leaves of the emerged transgenic stems into small 2 mm squares and place them in new selection medium, to achieve homoplasmy. Regenerate plants according to known methods.

It can be verified that plant cells produce light when grown on a medium containing hispidine.

Example 2. Preparation of the Plasmid Containing the H3H, Luz, CPH, HispS, NpgA Genes and the Sequences Allowing the Integration of these Genes into the Chloroplast Genome and their Expression The sequences of Luz, H3H, CPH, HispS, NpgA genes were adapted with chloroplast usage codons and then synthesized (SEQ ID NO: 1 to SEQ ID NO: 5 respectively). The selected promoters are SEQ ID NO: 9 to SEQ ID NO: 12 respectively and the terminators SEQ ID NO: 14 (Luz and HispS), SEQ ID NO: 15 (H3H), SEQ ID NO: 16 (CPH) and SEQ ID NO: 18 (NpgA).

The trnI and trnA sequences (SEQ ID NO: 6 and SEQ ID NO: 7) were chosen to allow the integration of the H3H and Luz genes into the chloroplast genome. They were amplified by PCR (Polymerase Chain Reaction) from chloroplast DNA of Nicotiana benthamiana. The spectinomycin/streptomycin resistance gene named aadA was amplified by PCR from a plasmid containing it (SEQ ID NO: 19).

An expression cassette was prepared as described above and integrated into a plasmid.

Chloroplast transformation was performed by biolistics on tobacco leaves, as described above.

Samples were recovered, cultured (several times to achieve homoplasmy) on medium containing spectinomycin.

One can thus verify that the cells produce light without the addition of an external compound.

Example 3 Obtaining Bioluminescent Chloroplasts (from Plant Cells Containing Bioluminescent Chloroplasts Chloroplasts of Nicotiana benthamiana leaves from shoots were visualized 15 weeks after transformation by bombardment.

For this purpose, several independent transformations were performed on different shoots of Nicotiana benthamiana. On two of them, leaf pieces were taken, which were mounted between slide and coverslip in a drop of sterile miliQ® water. As soon as the mounting was obtained, the samples were immediately visualized by microscopy.

Imaging was performed with a Nikon® Eclipse Ti microscope with a 100×1.49 NA immersion objective. The 405 nm laser (cw, Oxxius) was used to image the chloroplasts (10 W/cm$^2$). The emission from the samples was spectrally filtered using a dichroic mirror (Di01-R488-25x36, Semrock) and then imaged on a Hamamatsu EM-CCD camera (ImagEM). To detect bioluminescence, the 405 nm laser was blocked with a mechanical shutter. An additional lens was used to obtain a final magnification of 150× corresponding to a pixel size of 106.67 nm. The acquisition time was 1s.

The results obtained show that chloroplasts exhibit construct-related bioluminescence.

Taking into account the volume of a chloroplast (measurements made with the ImageJ software) which is on average 20 µM$^2$ and that a pixel has a surface of 0.01 µM$^2$, we can evaluate the global emission of a chloroplast. It is found that the number of photons per second per chloroplast is between 1600 and 3200.

The invention claimed is:

1. An autoluminescent *Nicotiana benthamiana* plant in which all cells comprising at least one chloroplast are such that the at least one chloroplast comprises 5 constructs each comprising a promoter operably linked to a nucleic acid encoding a protein, wherein the proteins are a *Neonothopanus nambi* hispidin-3-hydroxylase (H3H), a *N. nambi* luciferase (Luz), a *N. nambi* caffeoylpyruvate hydrolase (CPH), a *N. nambi* hispidin synthase (HispS), and an *Aspergillus nidulans* phosphopantetheinyl transferase (NpgA).

2. The autoluminescent plant according to claim 1, wherein the nucleic acids comprise codons adapted for expression in the at least one chloroplast.

3. The autoluminescent plant according to claim 1, wherein the promoters are selected from the group consisting of: SEQ ID NO:8, SEQ ID NO: 9, SEQ ID NO: 10, SEQ ID NO: 11, and SEQ ID NO:12.

4. The autoluminescent plant according to claim 1, wherein the constructs are integrated into the genome of the at least one chloroplast at trnI and trnA sites, represented by SEQ ID NO: 6 and SEQ ID NO: 7, respectively.

5. The autoluminescent plant according to claim 1, wherein the constructs have been integrated into the genome of the at least one chloroplast by homologous recombination.

6. A method of producing the autoluminescent plant according to claim 1, wherein the method comprises transforming chloroplasts of a *Nicotiana benthamiana* plant cell the 5 constructs and a 6ᵗʰ construct comprising a resistance gene selected from the group consisting of: nptII, badh, hph, aadA, cat, aphA6, aacCl, pat, gox, epsp, bxn and als, wherein the 6 constructs are inserted into the genome of the chloroplasts of plant cells by homologous recombination, producing callus from the transformed cell grown on a selective medium comprising:

an antibiotic selected from the group consisting of: neomycin, kanamycin, betain, hygromycin B, spectinomycin, streptomycin, chloramphenicol, amikacin, and gentamycin; or an herbicide selected from the group consisting of: bialophos, phosphinotricin, glufosinate, glyphosate, bromoxynil, sulfonylureas, imidazolines, triazolopyrimidines and pyrimidylbenzoates; and regenerating a plant from the callus.

7. The method according to claim 6, wherein transformation is performed by bombarding plant leaves using a particle gun.

8. The method according to claim 6, wherein transformation is performed by destabilizing plasma membranes with polyethylene glycol (PEG).

9. The method according to claim 6, wherein the resistance gene is aadA and the selective medium comprises spectinomycin and/or streptomycin.

10. A method of producing light, wherein the method comprises adding hispidin to a culture medium on which the autoluminescent plant according to claim 1 is growing.

*     *     *     *     *

SEQUENCE LISTING

```
<160> NUMBER OF SEQ ID NOS: 24

<210> SEQ ID NO 1
<211> LENGTH: 870
<212> TYPE: DNA
<213> ORGANISM: Artificial Sequence
<220> FEATURE:
<223> OTHER INFORMATION: squence Luz optimise
<220> FEATURE:
<221> NAME/KEY: Squence_codant_pour_His-tag
<222> LOCATION: (841)..(867)

<400> SEQUENCE: 1
atgtcaccac aaacagagac taaagcaagt gttggattca aaagaattaa tatttctttg      60
tcttcacttt ttgaaagatt gagcaagttg tcttcaagat caattgctat aacttgcgga     120
gttgttcttg cttctgctat agctttccca ataattagaa gagattatca aactttcttg     180
gaagttggac caagttatgc tccccaaaac ttcagagggt atattatagt ttgtgttctt     240
tctttgtttc gacaggaaca gaaaggactt gctatatatg atagattgcc tgaaaagagg     300
agatggttgg ctgaccttcc atttagggaa ggaactagac catcaattac tagtcatatt     360
atacaaagac agagaactca acttgttgat caagaattcg ctaccagaga acttattgat     420
aaggttattc caagagttca agctagacac actgacaaaa ctttcctttc aacctctaaa     480
ttcgagtttc atgctaaagc tatattcctt ttgccttcaa tacctattaa tgaccccttg     540
aatataccat ctcatgacac tgttagaaga accaaaagag aaattgcaca tatgcacgat     600
tatcacgatt gcactcttca tttggctctt gctgctcaag atggaaagga ggttttgaaa     660
aaagggtggg gacaaagaca tcccccttgct ggaccaggag ttccaggacc acctactgaa     720
tggactttcc tttatgctcc cagaaatgaa gaagaagcta gagttgttga aatgatagtt     780
```

-continued

```
gaagcttcta ttgggtatat gactaatgac ccagctggaa agattgttga aaatgctaag      840
ggatcttctc atcaccatca tcatcactga                                       870

<210> SEQ ID NO 2
<211> LENGTH: 1335
<212> TYPE: DNA
<213> ORGANISM: Artificial Sequence
<220> FEATURE:
<223> OTHER INFORMATION: squence H3h optimise
<220> FEATURE:
<221> NAME/KEY: Squence_codant_pour_His-tag
<222> LOCATION: (1306)..(1332)

<400> SEQUENCE: 2
atgtcaccac aaacagagac taaagcaagt gttggattca aagctagttt tgaaaactct       60
ctttcagttc ttatagttgg agctgggttg ggagggcttg ctgctgctat tgctcttaga      120
agacaaggac atgttgttaa aatttatgat tcttcaagtt ttaaggctga attgggagct      180
ggattggctg ttcctccaaa tactttgaga tctttacaac aacttggatg caacactgaa      240
aatcttaacg gagttgataa tctttgtttc actgctatgg gatatgatgg gtctgttgga      300
atgatgaaca atatgactga ttatagagaa gcttatggaa cttcatggat tatggttcat      360
agagttgatt tgcataatga attgatgaga gttgctcttg atccaggagg attgggacct      420
ccagctactt tgcatcttaa tcatagagtt actttctgcg atgttgatgc ttgcactgtt      480
actttcacta atggaactac tcaatcagct gatttgattg ttggagctga tgggattaga      540
tctactatta gaagattcgt tttggaagaa gatgttactg ttccagctag tgggatagtt      600
ggattcagat ggttggttca agctgatgct cttgatcctt atccagaatt ggattggata      660
gttaagaaac caccattggg agctagatta attagtactc ctcaaaaccc acaatctgga      720
gttggacttg ctgatagaag aactattata atatatgctt gcagaggagg gactatggtt      780
aacgttttgg ctgttcatga tgatgaaaga gatcaaaaca ctgctgattg gtctgttcca      840
gcttcaaaag atgatttgtt cagagttttc catgattatc atccaagatt cagaagactt      900
ttggaattag ctcaagatat aaacctttgg caaatgagag ttgttccagt tcttaaaaaa      960
tgggttaata aaagagtttg tttacttgga gatgctgctc atgcttctct tccaactttg     1020
ggacaagggt tcgggatggg attagaagat gctgttgctt taggaacttt gcttccaaag     1080
gggactaccg cttcacaaat agaaacccga ttggctgttt atgaacaact tagaaaggat     1140
cgagctgaat tcgttgctgc tgaatcatat gaagaacaat atgttccaga aatgcgagga     1200
ctttatctta gatcaaagga attgagagat cgagttatgg gttatgatat aaaagttgaa     1260
tcagaaaaag ttttagaaac tttgcttaga tcatctaact cagctggatc ttctcatcac     1320
catcatcatc actga                                                      1335

<210> SEQ ID NO 3
<211> LENGTH: 936
<212> TYPE: DNA
<213> ORGANISM: Artificial Sequence
<220> FEATURE:
<223> OTHER INFORMATION: squence cph optimise
<220> FEATURE:
<221> NAME/KEY: Squence_codant_pour_His-tag
<222> LOCATION: (907)..(933)

<400> SEQUENCE: 3
atgagaatca atcctactac ttctggttct ggggtttcca cggctcctat tagttcaact       60
```

-continued

```
tggtctagat taataagatt cgttgctatt gaaacttcat tagttcatat aggagaacca      120
atagatgcta ctatggatgt tggattagct agaagagaag gaaaaactat tcaagcttat      180
gaaataatag ggtctggatc agctttggat cttttctgctc aagtttctaa gaacgttctt      240
actgttagag aattgttaat gcctttgtca agagaagaaa taaaaactgt tagatgcttg      300
ggattgaatt atccagttca tgctactgaa gctaatgttg ctgttcctaa gtttccaaat      360
cttttctata aaccagttac ttcattgata ggaccagatg ggttaattac tataccttct      420
gttgttcaac cacctaaaga acatcaaagt gattatgaag ctgaacttgt tatagttata      480
ggtaaggctg ctaagaatgt ttctgaagat gaagctttgg attatgttct tggatatact      540
gctgctaatg acatttcatt tagaaagcat caattggctg tttctcaatg gagtttttca      600
aaaggattcg ggagtttact tttgactata agaatggctc aaactcattc tggaaacatt      660
aacagattca gtagagatca aatattcaat gttaaaaaga ctatttcatt tttatctcaa      720
ggtactactt tggaaccagg atcaataata ttaactggaa ctccagatgg ggttggattt      780
gttagaaacc cacctctttta tttgaaggat ggtgatgaag ttatgacttg gattggatct      840
ggaattggga ctttagctaa tactgttcaa gaagaaaaaa cttgtttttgc tagtgggggga      900 catgaaggat cttctcatca ccatcatcat cactga                               936
```

```
<210> SEQ ID NO 4
<211> LENGTH: 5103
<212> TYPE: DNA
<213> ORGANISM: Artificial Sequence
<220> FEATURE:
<223> OTHER INFORMATION: squence HispS optimise
<220> FEATURE:
<221> NAME/KEY: Squence_codant_pour_His-tag
<222> LOCATION: (5074)..(5100)

<400> SEQUENCE: 4
```

```
atgtcaccac aaacagagac taaagcaagt gttggattca aaaattcttc aaagaatcct      60
ccatcaactt tgttggatgt tttcttggat actgctagaa accttgatac tgctttgaga      120
aacgttcttg aatgcggaga acatagatgg agttatagag aattggatac tgtttcaagt      180
gctcttgctc aacatcttag atatactgtt ggattgtctc ctactgttgc tgttatatct      240
gaaaaccatc catatatatt agctcttatg ctggctgttt ggaagttagg agggactttt      300
gctcctattg atgttcattc tcctgctgaa ttagttgctg ggatgttgaa tattgttagt      360
ccaagttgtc ttgttatacc ttctagtgat gttactaacc aaactcttgc ttgcgatctt      420
aacatacctg ttgttgcttt ccatcctcat caatctacta taccagaatt gaataagaaa      480
tatcttactg attcacaaat atctcctgat ttgccatttt ctgatcctaa tagacctgct      540
ttgtatcttt tcacttcttc agctacttct agaagtaact taaaatgcgt tcctttgact      600 catacttttta tacttagaaa ctctctttca aagagagctt ggtgtaaaag aatgagacca      660
gaaaccgatt ttgatgggat tagagttttg ggatgggctc cttggtctca tgttcttgct      720
catatgcaag atattggacc tttgactctt ttgaatgctg ggtgctatgt tttcgctact      780
actccttcaa cttatcctac tgaattgaaa gatgatagag atttgatatc ttgtgctgct      840
aacgctatta tgtataaggg ggttaaaagt tttgcttgct taccattcgt tcttggggggg      900 ttgaaggctc tttgcgaatc tgaaccaagt gttaaggctc atttgcaagt tgaagaaaga      960
gctcaattgt tgaagagcct ccagcacatg gaaatcttgg aatgcggagg agctatgtta     1020
gaagcttctg ttgcttcttg ggctattgaa aattgcattc tatatctat aggaattggg      1080
```

-continued

```
atgactgaaa ctggaggggc tttatttgct gggcctgtac aagctataaa gactggattc      1140
tcttcagaag ataagtttat tgaagatgct acttatttac ttgtaaaaga tgatcatgaa      1200
tctcatgctg aagaagatat aaatgaagga gaacttgttg taaaaagtaa gatgttgcct      1260
agaggatatt tggggtatag tgatccatct ttttcagtag atgatgctgg gtgggtaact      1320
tttagaactg gggatagata ttctgtaact ccagatggaa agtttagttg gttggggaga      1380
aacactgatt ttatacagat gacttcagga gaaacttag atcctagacc aattgaaagt      1440
tcattgtgtg aatcatcatt gatatcaaga gcttgcgtaa taggggataa gtttcttaat      1500
ggacctgctg ctgctgtttg tgctattata gaattagaac caactgctgt tgaaaaagga      1560
caagctcata gtagagaaat agctagagtt tttgctccaa ttaatagaga tcttccacca      1620
cctttgagaa tagcttggag tcatgtatta gtacttcaac ctagtgaaaa aatacctatg      1680
actaaaaagg ggaccatttt cagaaagaaa attgaacaag ttttcgggtc tgctttggga      1740
ggatcttcag gagataattc acaagcaact gctgatgctg gggttgtaag aagagatgaa      1800
ttgtcaaaca ctgttaaaca tattatatca agagttcttg gagtatctga tgatgaattg      1860
ctttggaccc ttagtttcgc tgaattagga atgactagtg ctcttgctac tagaattgct      1920
aatgaactta atgaagtatt agttggtgtt aacttaccaa taaatgcttg ctatattcat      1980
gttgatcttc ctagtttatc aaacgctgta tatgctaagt tggctcattt aaaacttcca      2040
gatagaactc cagaaccaag acaagctcca gttgaaaact caggaggtaa agaaatagtt      2100
gttgttgggc aagctttcag acttcctggg tcaattaacg atgttgcatc attaagagat      2160
gctttcttag ctagacaagc aagttcaata attactgaaa taccatcaga tagatgggat      2220
catgcttcat tctaccctaa agatataaga tttaataaag ctggtttagt tgatatagct      2280
aattatgatc attcattctt tgggttgacc gcaactgaag ctttgtatct ttcacctacc      2340
atgagacttg ctttggaagt atcatttgaa gctttggaaa acgctaacat accagtttca      2400
caattaaagg gtagtcaaac tgctgtatat gttgcaacca ctgacgatgg gtttgagacg      2460
ctcttaaacg ctgaagctgg ttatgatgca tatactagat tctatggaac tgggagagca      2520
gcttctaccg cttctggaag aattagttgt ttattggatg tacatggacc atcaattact      2580
gttgatactg cttgctctgg aggggctgta tgtattgatc aagctataga ttatttgcaa      2640
agttcatctg ctgctgatac tgcaattata tgtgcttcaa atactcattg ctggccaggg      2700
tcattcagat tcctttctgc tcaaggaatg gtttcaccag gaggaagatg tgctactttt      2760
actaccgatg ctgatgggta tgttccaagt gagggtgctg ttgctttcat tttaaaaact      2820
agagaagctg ctatgagaga taaggatact atattggcta ctattaaagc tactcaaatt      2880
agtcataacg ggagaagtca aggtttggtt gctccaaacg taaatagtca agctgattta      2940
catagatcac ttttgcaaaa ggctggtttg agtccagctg atataagatt cattgaagct      3000
catgggaccg gaaccagtct tggggattta tcagaaattc aagctattaa cgatgcttat      3060
acttcttcac aacctagaac cactggacca ttaattgttt cagctagtaa aactgttatt      3120
gggcatactg aacctgctgg acctcttgtt gggatgcttt cagtattgaa ctcattcaag      3180
gaaggggctg tacctgggct tgctcatttg actgctgata acttaaatcc atcacttgat      3240
tgctcatctg tacctttgct tataccttat caacctgttc atttggctgc tccaaaacct      3300
catagagctg ctgttagaag ttatggattt agtgggacct ggggggggaat tgtacttgaa      3360 gctcctgatg aagaaagatt agaagaagaa cttccaaacg ataaacctat gttatttgtt      3420
gtatctgcta aaacccatac cgctttgatt gaatatttgg gaagatatct tgaattttta      3480
```

```
ttacaagcta acccacaaga tttttgcgat atatgttata cctcttgcgt agggagagaa   3540
cattatagat atagatatgc ttgtgttgct aacgatatgg aagatcttat tgggcaatta   3600
caaaagagac ttggaagtaa ggttccacct aagccttcat ataagagagg ggctttggct   3660
tttgctttct caggacaagg gacccaattc agagggatgg ctactgaatt ggctaaagct   3720
tatagtgggt tcagaaagat agtttctgat ttggctaaaa gagctagtga acttagtggt   3780
catgctattg atagattctt gcttgcttat gatataggtg cagaaaacgt agcaccagat   3840
agtgaagcag atcaaatttg catattcgta tatcaatgca gtgttcttag atggttgcaa   3900
accatgggaa taagaccatc agctgttata gggcattcat tgggagaaat atctgcttca   3960
gtagctgctg gggctttgtc acttgatagt gctttggatt tagtaattag tagagctaga   4020
ttgttaagaa gttcagcttc agctcctgca ggaatggctg caatgtcagc tagtcaagat   4080
gaagttgtag aacttatagg aaagttggat cttgataaag ctaattctct ttcagtatca   4140
gtaattaacg ggcctcaaaa cactgttgtt tctgggtcaa gtgctgctat agaatcaatt   4200
gtagctcttg ctaagggtag aaaaattaag gctagtgctc ttaacattaa ccaagctttc   4260
cactcaccat atgtagatag tgctgtacca ggattaagag cttggtcaga aaaacatata   4320
tcatctgcta gaccattaca aattccactt tattcaactt tacttggtgc tcaaatttca   4380
gaaggagaaa tgcttaaccc agatcattgg gttgatcatg ctagaaaacc tgtacaattc   4440
gctcaagctg ctactaccat gaaggaatca tttaccggag taattataga tataggacca   4500
caagttgtag cttggtcatt gttgctttct aatgggttaa cctcagttac cgctttggct   4560
gctaagagag ggagatcaca acaagttgct ttcttgtcag ctttagctga tctttatcaa   4620
gattatgggg ttgtacctga tttttgttgga ttatatgctc aacaagaaga tgcttcaaga   4680
ttaaagaaaa ctgatattct tacctatcct tttcaaagag gtgaagaaac tctttcatct   4740
gggtcatcta ctccaacctt agaaaacacc gatttagata gtggtaaaga gttacttatg   4800
gggcctacca gagggctttt gagagctgat gatttgagag attctattgt tagtagtgtt   4860
aaggatgttt tggaacttaa atcaaacgaa gatttggatc tttcagaatc tcttaatgct   4920
ttggggatgg attcaattat gtttgctcaa ttaagaaaga gaattggaga aggattaggg   4980
ttgaatgtac caatggtatt cttgtctgat gcattttcta taggggaaat ggttagtaat   5040
ttggtagaac aagctgaagc ttcagaagat aacggatctt ctcatcacca tcatcatcac   5100
tga                                                                  5103
```

```
<210> SEQ ID NO 5
<211> LENGTH: 1101
<212> TYPE: DNA
<213> ORGANISM: Artificial Sequence
<220> FEATURE:
<223> OTHER INFORMATION: gne NpgA optimis
<220> FEATURE:
<221> NAME/KEY: Squence_codant_pour_His-tag
<222> LOCATION: (1072)..(1098)

<400> SEQUENCE: 5
```

```
atgtcaccac aaacagagac taaagcaagt gttggattca aagttcaaga tacttcatct     60
gctagtactt ctccaatttt gactagatgg tatatagata ctagacctttt aactgcttct    120 actgctgctt taccactttt ggaaactttg caacctgctg atcaaatatc tgttcaaaag    180
tattatcatt tgaaagataa acacatgtca ttagcttcaa atttgcttaa atatttattc    240
gttcatagaa actgcagaat tccatggtca tctatagtta tatcaagaac tcctgatcct    300
```

```
catagaagac cttgctatat tccaccttca gggtctcaag aagattcttt taaggatgga        360
tatactggga taaacgttga attcaacgtt tctcatcaag ctagtatggt tgctatagct        420
ggaactgctt ttactcctaa ttctggggga gattctaagt taaaaccaga agttggaata        480
gatattactt gtgttaatga aagacaagga agaaatggag aagaagaag tttggaatca         540 ttgagacaat atattgatat atttagtgaa gttttttcaa ctgctgaaat ggctaatatt        600
agaagattag atggagtttc atctagttct ttatcagctg atagattggt tgattatgga        660
tatagattat tttatactta ttgggctctt aaggaagctt atataaaaat gactgggggaa       720 gctttgttag ctccttggtt gagagaactt gaatttagta acgttgttgc tccagctgct        780
gttgctgaat ctggggattc agctggagat ttcggagaac catatactgg ggttagaact        840
actctttata agaatcttgt ggaagatgtt agaatagaag ttgctgcttt aggggggagat       900 tatttgtttg ctactgctgc tagaggggga ggaattgggg cttcatctag acctggaggg        960
ggaccagatg gatcagggat aagatcacaa gatccatgga gaccatttaa aaagcttgat       1020
attgaaagag atattcaacc atgcgctact ggagtttgta actgtctttc aggatcttct       1080
catcaccatc atcatcactg a                                                 1101
```

```
<210> SEQ ID NO 6
<211> LENGTH: 1989
<212> TYPE: DNA
<213> ORGANISM: Nicotiana benthamiana

<400> SEQUENCE: 6
```

```
taccaagctg gagtacggta ggggcagagg gaatttccgg tggagcggtg aaatgcgtag         60
agatcggaaa gaacaccaac ggcgaaagca ctctgctggg ccgacactga cactgagaga        120
cgaaagctag gggagcgaat gggattagat accccagtag tcctagccgt aaacgatgga        180
tactaggcgc tgtgcgtatc gacccgtgca gtgctgtagc taacgcgtta agtatcccgc        240
ctggggagta cgttcgcaag aatgaaactc aaaggaattg acgggggccc gcacaagcgg        300
tggagcatgt ggtttaattc gatgcaaagc gaagaacctt accagggctt gacatgccgc        360
gaatcctctt gaaagagagg ggtgccttcg ggaacgcgga cacaggtggt gcatggctgt        420
cgtcagctcg tgccgtaagg tgttgggtta agtcccgcaa cgagcgcaac cctcgtgttt        480
agttgccatc gttgagtttg gaaccctgaa cagactgccg gtgataagcc ggaggaaggt        540
gaggatgacg tcaagtcatc atgcccctta tgccctgggc gacacacgtg ctacaatggc        600
cgggacaaag ggtcgcgatc ccgcgagggt gagctaacct caaaaacccg tcctcagttc        660
ggattgcagg ctgcaactcg cctgcatgaa gccggaatcg ctagtaatcg ccggtcagcc        720
atacggcggt gaattcgttc ccgggccttg tacacaccgc ccgtcacact atgggagctg        780
gccatgcccg aagtcgttac cttaaccgca aggaggggga tgccgaaggc agggctagtg        840
actggagtga agtcgtaaca aggtagccgt actggaaggt gcggctggat cacctccttt        900
tcagggagag ctaatgcttg ttgggtattt tggtttgaca ctgcttcaca cccccaaaaa        960
aaaagaaggg agctacgtct gagttaaact tggagatgga agtcttcttt cctttctcga       1020
cggtgaagta agaccaagct catgagctta ttatcctagg tcggaacaag ttgataggac       1080 ccccttttttt acgtccccat gttccccccg tgtggcgaca tgggggcgaa aaaaggaaag      1140
agagggatgg ggtttctctc gctttttggca tagcgggccc ccagtgggag gctcgcacga     1200
cgggctatta gctcagtggt agagcgcgcc cctgataatt gcgtcgttgt gcctgggctg      1260
```

-continued

```
tgagggctct cagccacatg gatagttcaa tgtgctcatc ggcgcctgac cctgagatgt   1320
ggatcatcca aggcacatta gcatggcgta ctcctcctgt tcgaaccggg gtttgaaacc   1380
aaactcctcc tcaggaggat agatggggcg attcgggtga gatccaatgt agatccaact   1440
ttcgattcac tcgtgggatc cgggcggtcc gggggggacc accacggctc ctctcttctc   1500
gagaatccat acatccctta tcagtgtatg gacagctatc tctcgagcac aggtttaggt   1560
tcggcctcaa tggaaaaata aaatggagca cctaacaacg catcttcaca gaccaagaac   1620
tacgagatcg cccctttcat tctggggtga cggagggatc gtaccattcg agccgttttt   1680
ttcttgactc gaaatgggag caggtttgaa aaaggatctt agagtgtcta gggttgggcc   1740
aggagggtct cttaacgcct tctttttttct tctcatcgga gttatttcac aaagacttgc   1800
cagggtaagg aagaaggggg gaacaagcac acttggagag cgcagtacaa cggagagttg   1860
tatgctgcgt tcgggaagga tgaatcgctc ccgaaaagga atctattgat tctctcccaa   1920
ttggttggac cgtaggtgcg atgatttact tcacgggcga ggtctctggt tcaagtccag   1980
gatggccca                                                            1989
```

<210> SEQ ID NO 7
<211> LENGTH: 1900
<212> TYPE: DNA
<213> ORGANISM: Nicotiana benthamiana

<400> SEQUENCE: 7

```
gcgccaggga aaagaataga agaagcatct gactacttca tgcatgctcc acttggctcg     60
gggggatata gctcagttgg tagagctccg ctcttgcaat tgggtcgttg cgattacggg    120
ttggatgtct aattgtccag gcggtaatga tagtatcttg tacctgaacc ggtggctcac    180
tttttctaag taatggggaa gaggaccgaa acgtgccact gaaagactct actgagacaa    240
agatgggctg tcaagaacgt agaggaggta ggatgggcag ttggtcagat ctagtatgga    300
tcgtacatgg acggtagttg gagtcggcgg ctctcccagg gttccctcat ctgagatctc    360
tggggaagag gatcaagttg gcccttgcga acagcttgat gcactatctc ccttcaaccc    420
tttgagcgaa atgcggcaaa agaaaaggaa ggaaaatcca tggaccgacc catcatctc     480 caccccgtag gaactacgag atcaccccaa ggacgccttc ggcatccagg ggtcacggac    540
cgaccataga accctgttca ataagtggaa cgcattagct gtccgctctc aggttgggca    600
gtcagggtcg gagaagggca atgactcatt cttagttaga atgggattcc aactcagcac    660
cttttgagtg agattttgag aagagttgct cttttggagag cacagtacga tgaaagttgt    720
aagctgtgtt cggggggggag ttattgtcta tcgttggcct ctatggtaga atcagtcggg    780
ggacctgaga ggcggtggtt taccctgcgg cggatgtcag cggttcgagt ccgcttatct    840
ccaactcgtg aacttagccg atacaaagct ttatgatagc acccaatttt tccgattcgg    900
cggttcgatc tatgatttat cattcatgga cgttgataag atccatccat ttagcagcac    960
cttaggatgg catagcctta aaagtgaagg gcgaggttca aacgaggaaa ggcttacggt   1020
ggatacctag gcacccagag acgaggaagg gcgtagtaat cgacgaaatg cttcggggag   1080
ttgaaaataa gcatagatcc ggagattccc gaatagggca acctttcgaa ctgctgctga   1140
atccatgggc aggcaagaga caacctggcg aactgaaaca tcttagtagc cagaggaaaa   1200
gaaagcaaaa gcgattcccg tagtagcggc gagcgaaatg ggagcagcct aaaccgtgaa   1260
aacggggttg tgggagagca atacaagcgt cgtgctgcta ggcgaagcag cccgaatgct   1320
gcaccctaga tggcgaaagt ccagtagccg aaagcatcac tagcttatgc tctgacccga   1380
```

```
gtagcatggg gcacgtggaa tcccgtgtga atcagcaagg accaccttgc aaggctaaat    1440
actcctgggt gaccgatagc gaagtagtac cgtgagggaa gggtgaaaag aacccccatc    1500
ggggagtgaa atagaacatg aaaccgtaag ctcccaagca gtgggaggag ccagggctct    1560
gaccgcgtgc ctgttgaaga atgagccggc gactcatagg cagtggcttg gttaagggaa    1620
cccaccggag ccgtagcgaa agcgagtctt catagggcaa ttgtcactgc ttatggaccc    1680
gaacctgggt gatctatcca tgaccaggat gaagcttggg tgaaactaag tggaggtccg    1740
aaccgactga tgttgaagaa tcagcggatg agttgtggtt aggggtgaaa tgccactcga    1800
acccagagct agctggttct ccccgaaatg cgttgaggcg cagcagttga ctggacatct    1860
aggggtaaag cactgtttcg gtgcgggccg cgagagcggt                          1900
```

```
<210> SEQ ID NO 8
<211> LENGTH: 234
<212> TYPE: DNA
<213> ORGANISM: Artificial Sequence
<220> FEATURE:
<223> OTHER INFORMATION: promoteur Prrn optimis
<220> FEATURE:
<221> NAME/KEY: promoteur
<222> LOCATION: (1)..(219)
<220> FEATURE:
<221> NAME/KEY: 5'UTR
<222> LOCATION: (220)..(234)

<400> SEQUENCE: 8
atcagttcga gcctgattat ccctaagccc aatgtgagtt tttctagttg gatttgctcc      60
cccgccgtcg ttcaatgaga atggataaga ggctcgtggg attgacgtga gggggcaggg     120
atggctatat ttctgggagc gaactccggg cgaatatgaa gcgcatggat acaagttatg     180
ccttggaatg aaagacaatt ccgaatccgc tttgtctacg aaggagatag aacc           234
```

```
<210> SEQ ID NO 9
<211> LENGTH: 334
<212> TYPE: DNA
<213> ORGANISM: Artificial Sequence
<220> FEATURE:
<223> OTHER INFORMATION: promoteur PpsbA optimis
<220> FEATURE:
<221> NAME/KEY: promoteur
<222> LOCATION: (1)..(276)
<220> FEATURE:
<221> NAME/KEY: 5'UTR
<222> LOCATION: (277)..(334)

<400> SEQUENCE: 9
atccaagaaa agtgagctat taacgcgtcc tattttaata ctccgaagga ggcagttggc      60
aggcaactgc cactgacgtc ccgtaagggt aaggggacgt ccactggcgt cccgtaaggg     120
gaaggggacg taggtacata aatgtgctag gtaactaacg tttgattttt tgtggtataa     180
tatatgtacc atgcttttaa tagaagcttg aatttataaa ttaaaatatt tttacaatat     240
tttacggaga aattaaaact ttaaaaaaat taacatgtcg agtagacctt gttgttgtga     300
gaattcttaa ttcatgagtt gtagggaggg attt                                 334
```

```
<210> SEQ ID NO 10
<211> LENGTH: 379
<212> TYPE: DNA
<213> ORGANISM: Artificial Sequence
<220> FEATURE:
<223> OTHER INFORMATION: promoteur PrbcL optimis
<220> FEATURE:
```

```
<221> NAME/KEY: promoteur
<222> LOCATION: (1)..(289)
<220> FEATURE:
<221> NAME/KEY: 5'UTR
<222> LOCATION: (290)..(379)

<400> SEQUENCE: 10
aattccgtat attttcacat ctaggattta catatacaac atataccact gtcaaggggg      60
aagttcttat tatttaggtt agtcaggtat ttccatttca aaaaaaaaaa aagtaaaaaa     120
gaaaaattgg gttgcgctat atatatgaaa gagtatacaa taatgatgta tttggcaaat     180
caaataccat ggtctaataa tcaaacattc tgattagttg ataatattag tattagttgg     240
aaattttgtg aaagattcct atgaaaagtt tcattaacac ggaattcgtg aattaaccga     300
tcgacgtgca agcggacatt tattttaaat tcgataattt ttgcaaaaac atttcgacat     360
atttatttat tttattatt                                                  379

<210> SEQ ID NO 11
<211> LENGTH: 277
<212> TYPE: DNA
<213> ORGANISM: Artificial Sequence
<220> FEATURE:
<223> OTHER INFORMATION: promoteur Prrn optimis
<220> FEATURE:
<221> NAME/KEY: promoteur
<222> LOCATION: (1)..(219)
<220> FEATURE:
<221> NAME/KEY: 5'UTR
<222> LOCATION: (220)..(277)

<400> SEQUENCE: 11
atcagttcga gcctgattat ccctaagccc aatgtgagtt tttctagttg gatttgctcc      60
cccgccgtcg ttcaatgaga atggataaga ggctcgtggg attgacgtga gggggcaggg     120
atggctatat ttctgggagc gaactccggg cgaatatgaa gcgcatggat acaagttatg     180
ccttggaatg aaagacaatt ccgaatccgc tttgtctacg tcgagtagac cttgttgttg     240
tgagaattct taattcatga gttgtaggga gggattt                              277

<210> SEQ ID NO 12
<211> LENGTH: 306
<212> TYPE: DNA
<213> ORGANISM: Artificial Sequence
<220> FEATURE:
<223> OTHER INFORMATION: Promoteur PatpI optimis
<220> FEATURE:
<221> NAME/KEY: promoteur
<222> LOCATION: (1)..(248)
<220> FEATURE:
<221> NAME/KEY: 5'UTR
<222> LOCATION: (249)..(306)

<400> SEQUENCE: 12
tctagctata taagaaatcc ttgattaata ataacataat aagataaata acttacttca      60
gaaatccctt atggaatcgc ttactatttc tgaatttcaa aaaagagata aaaatagctg     120
gggatattat gtgatttatt agtattctaa atcttagttg gtattcaaaa tatccgattc     180
aagtagacaa agagatggtt gaatcaaaaa attttgttta aagttcaatt ttttcagagg     240
gcaaggcagt cgagtagacc ttgttgttgt gagaattctt aattcatgag ttgtagggag     300
ggattt                                                                306

<210> SEQ ID NO 13
<211> LENGTH: 227
```

<212> TYPE: DNA
<213> ORGANISM: Artificial Sequence
<220> FEATURE:
<223> OTHER INFORMATION: terminateur TpsbA optimis

<400> SEQUENCE: 13
ctagagatcc tggcctagtc tataggaggt tttgaaaaga aaggagcaat aatcatttc      60 ttgttctatc aagagggtgc tattgctcct ttcttttttt ctttttattt atttactagt     120
attttactta catagacttt tttgtttaca ttatagaaaa agaaggagag gttattttct     180
tgcatttatt catgattgag tattctattt tgattttgta tttgttt                  227

<210> SEQ ID NO 14
<211> LENGTH: 169
<212> TYPE: DNA
<213> ORGANISM: Artificial Sequence
<220> FEATURE:
<223> OTHER INFORMATION: terminateur Trps16 optimis

<400> SEQUENCE: 14
tcaaccgaaa ttcaattaag gaaataaatt aaggaaatac aaaaaggggg gtagtcattt      60
gtatataact ttgtatgact tttctcttct attttttttgt atttcctccc tttccttttc    120
tatttgtatt ttttttatcat tgcttccatt gaattccgtg ttctataac                169

<210> SEQ ID NO 15
<211> LENGTH: 173
<212> TYPE: DNA
<213> ORGANISM: Artificial Sequence
<220> FEATURE:
<223> OTHER INFORMATION: terminateur TrbcL optimis

<400> SEQUENCE: 15
taaaaacagt agacattagc agataaatta gcaggaaata aagaaaggat aaggagaaag      60
aactcaagta attatccttc gttctcttaa ttgaattgca attaaactcg gcccaatctt     120
ttactaaaag gattgagccg aatacaacaa agattctatt gcatatattt tga            173

<210> SEQ ID NO 16
<211> LENGTH: 218
<212> TYPE: DNA
<213> ORGANISM: Artificial Sequence
<220> FEATURE:
<223> OTHER INFORMATION: terminateur TrrnB optimis

<400> SEQUENCE: 16
atcaaataaa acgaaaggct cagtcgaaag actgggcctt tcgttttatc tgttgtttgt      60
cggtgaacgc tctcctgagt aggacaaatc cgccgggagc ggatttgaac gttgcgaagc    120
aacggcccgg agggtggcgg gcaggacgcc cgccataaac tgccaggctc aaattaagca    180
gaaggccatc ctgacggatg gcctttttgc gtttctac                            218

<210> SEQ ID NO 17
<211> LENGTH: 228
<212> TYPE: DNA
<213> ORGANISM: Artificial Sequence
<220> FEATURE:
<223> OTHER INFORMATION: terminateur TpsbA optimis

<400> SEQUENCE: 17
tctagagatc ctggcctagt ctataggagg ttttgaaaag aaaggagcaa taatcatttt      60
cttgttctat caagagggtg ctattgctcc tttcttttttt tcttttttatt tatttactag    120

-continued

```
tattttactt acatagactt ttttgtttac attatagaaa aagaaggaga ggttattttc      180
ttgcatttat tcatgattga gtattctatt ttgattttgt atttgttt                   228
```

<210> SEQ ID NO 18
<211> LENGTH: 222
<212> TYPE: DNA
<213> ORGANISM: Artificial Sequence
<220> FEATURE:
<223> OTHER INFORMATION: terminateur TpsbA optimis

<400> SEQUENCE: 18

```
gatcctggcc tagtctatag gaggttttga aaagaaagga gcaataatca ttttcttgtt       60
ctatcaagag ggtgctattg ctcctttctt tttttctttt tatttattta ctagtatttt      120
acttacatag actttttttgt ttacattata gaaaaagaag gagaggttat tttcttgcat      180
ttattcatga ttgagtattc tattttgatt ttgtatttgt tt                         222
```

<210> SEQ ID NO 19
<211> LENGTH: 792
<212> TYPE: DNA
<213> ORGANISM: Artificial Sequence
<220> FEATURE:
<223> OTHER INFORMATION: gne aad optimis

<400> SEQUENCE: 19

```
atgggggaag cggtgatcgc cgaagtatcg actcaactat cagaggtagt tggcgtcatc       60
gagcgccatc tcgaaccgac gttgctggcc gtacatttgt acggctccgc agtggatggc      120
ggcctgaagc cacacagtga tattgatttg ctggttacgg tgaccgtaag gcttgatgaa      180
acaacgcggc gagctttgat caacgacctt ttggaaactt cggcttcccc tggagagagc      240
gagattctcc gcgctgtaga agtcaccatt gttgtgcacg acgacatcat tccgtggcgt      300
tatccagcta agcgcgaact gcaatttgga gaatggcagc gcaatgacat tcttgcaggt      360
atcttcgagc cagccacgat cgacattgat ctggctatct tgctgacaaa agcaagagaa      420
catagcgttg ccttggtagg tccagcggcg gaggaactct ttgatccggt tcctgaacag      480
gatctatttg aggcgctaaa tgaaacctta acgctatgga actcgccgcc cgactgggct      540
ggcgatgagc gaaatgtagt gcttacgttg tcccgcattt ggtacagcgc agtaaccggc      600
aaaatcgcgc cgaaggatgt cgctgccgac tgggcaatgg agcgcctgcc ggcccagtat      660
cagcccgtca tacttgaagc tagacaggct tatcttggac aagaagaaga tcgcttggcc      720
tcgcgcgcag atcagttgga agaatttgtc cactacgtga aaggcgagat caccaaggta      780
gtcggcaaat ga                                                          792
```

<210> SEQ ID NO 20
<211> LENGTH: 289
<212> TYPE: PRT
<213> ORGANISM: Artificial Sequence
<220> FEATURE:
<223> OTHER INFORMATION: Drive de Luz de Neonothopanus nambi
<220> FEATURE:
<221> NAME/KEY: His-tag
<222> LOCATION: (281)..(289)

<400> SEQUENCE: 20

```
Met Ser Pro Gln Thr Glu Thr Lys Ala Ser Val Gly Phe Lys Arg Ile
1               5                   10                  15

Asn Ile Ser Leu Ser Ser Leu Phe Glu Arg Leu Ser Lys Leu Ser Ser
            20                  25                  30
```

-continued

```
Arg Ser Ile Ala Ile Thr Cys Gly Val Val Leu Ala Ser Ala Ile Ala
        35              40              45

Phe Pro Ile Ile Arg Arg Asp Tyr Gln Thr Phe Leu Glu Val Gly Pro
    50              55              60

Ser Tyr Ala Pro Gln Asn Phe Arg Gly Tyr Ile Ile Val Cys Val Leu
65              70              75              80

Ser Leu Phe Arg Gln Glu Gln Lys Gly Leu Ala Ile Tyr Asp Arg Leu
                85              90              95

Pro Glu Lys Arg Arg Trp Leu Ala Asp Leu Pro Phe Arg Glu Gly Thr
            100             105             110

Arg Pro Ser Ile Thr Ser His Ile Ile Gln Arg Gln Arg Thr Gln Leu
            115             120             125

Val Asp Gln Glu Phe Ala Thr Arg Glu Leu Ile Asp Lys Val Ile Pro
    130             135             140

Arg Val Gln Ala Arg His Thr Asp Lys Thr Phe Leu Ser Thr Ser Lys
145             150             155             160

Phe Glu Phe His Ala Lys Ala Ile Phe Leu Leu Pro Ser Ile Pro Ile
                165             170             175

Asn Asp Pro Leu Asn Ile Pro Ser His Asp Thr Val Arg Arg Thr Lys
            180             185             190

Arg Glu Ile Ala His Met His Asp Tyr His Asp Cys Thr Leu His Leu
            195             200             205

Ala Leu Ala Ala Gln Asp Gly Lys Glu Val Leu Lys Lys Gly Trp Gly
    210             215             220

Gln Arg His Pro Leu Ala Gly Pro Gly Val Pro Gly Pro Pro Thr Glu
225             230             235             240

Trp Thr Phe Leu Tyr Ala Pro Arg Asn Glu Glu Glu Ala Arg Val Val
                245             250             255

Glu Met Ile Val Glu Ala Ser Ile Gly Tyr Met Thr Asn Asp Pro Ala
            260             265             270

Gly Lys Ile Val Glu Asn Ala Lys Gly Ser Ser His His His His His
        275             280             285

His
```

```
<210> SEQ ID NO 21
<211> LENGTH: 444
<212> TYPE: PRT
<213> ORGANISM: Artificial Sequence
<220> FEATURE:
<223> OTHER INFORMATION: Drive de H3H de Neonothopanus nambi
<220> FEATURE:
<221> NAME/KEY: His-tag
<222> LOCATION: (436)..(444)

<400> SEQUENCE: 21
```

```
Met Ser Pro Gln Thr Glu Thr Lys Ala Ser Val Gly Phe Lys Ala Ser
1               5               10              15

Phe Glu Asn Ser Leu Ser Val Leu Ile Val Gly Ala Gly Leu Gly Gly
            20              25              30

Leu Ala Ala Ala Ile Ala Leu Arg Arg Gln Gly His Val Val Lys Ile
        35              40              45

Tyr Asp Ser Ser Ser Phe Lys Ala Glu Leu Gly Ala Gly Leu Ala Val
    50              55              60

Pro Pro Asn Thr Leu Arg Ser Leu Gln Gln Leu Gly Cys Asn Thr Glu
65              70              75              80

Asn Leu Asn Gly Val Asp Asn Leu Cys Phe Thr Ala Met Gly Tyr Asp
```

-continued

```
                    85              90              95

Gly Ser Val Gly Met Met Asn Asn Met Thr Asp Tyr Arg Glu Ala Tyr
            100             105             110

Gly Thr Ser Trp Ile Met Val His Arg Val Asp Leu His Asn Glu Leu
            115             120             125

Met Arg Val Ala Leu Asp Pro Gly Gly Leu Gly Pro Pro Ala Thr Leu
    130             135             140

His Leu Asn His Arg Val Thr Phe Cys Asp Val Asp Ala Cys Thr Val
145             150             155             160

Thr Phe Thr Asn Gly Thr Thr Gln Ser Ala Asp Leu Ile Val Gly Ala
            165             170             175

Asp Gly Ile Arg Ser Thr Ile Arg Arg Phe Val Leu Glu Glu Asp Val
            180             185             190

Thr Val Pro Ala Ser Gly Ile Val Gly Phe Arg Trp Leu Val Gln Ala
            195             200             205

Asp Ala Leu Asp Pro Tyr Pro Glu Leu Asp Trp Ile Val Lys Lys Pro
    210             215             220

Pro Leu Gly Ala Arg Leu Ile Ser Thr Pro Gln Asn Pro Gln Ser Gly
225             230             235             240

Val Gly Leu Ala Asp Arg Arg Thr Ile Ile Ile Tyr Ala Cys Arg Gly
            245             250             255

Gly Thr Met Val Asn Val Leu Ala Val His Asp Asp Glu Arg Asp Gln
            260             265             270

Asn Thr Ala Asp Trp Ser Val Pro Ala Ser Lys Asp Asp Leu Phe Arg
            275             280             285

Val Phe His Asp Tyr His Pro Arg Phe Arg Arg Leu Leu Glu Leu Ala
    290             295             300

Gln Asp Ile Asn Leu Trp Gln Met Arg Val Val Pro Val Leu Lys Lys
305             310             315             320

Trp Val Asn Lys Arg Val Cys Leu Leu Gly Asp Ala Ala His Ala Ser
            325             330             335

Leu Pro Thr Leu Gly Gln Gly Phe Gly Met Gly Leu Glu Asp Ala Val
            340             345             350

Ala Leu Gly Thr Leu Leu Pro Lys Gly Thr Thr Ala Ser Gln Ile Glu
            355             360             365

Thr Arg Leu Ala Val Tyr Glu Gln Leu Arg Lys Asp Arg Ala Glu Phe
    370             375             380

Val Ala Ala Glu Ser Tyr Glu Glu Gln Tyr Val Pro Glu Met Arg Gly
385             390             395             400

Leu Tyr Leu Arg Ser Lys Glu Leu Arg Asp Arg Val Met Gly Tyr Asp
            405             410             415

Ile Lys Val Glu Ser Glu Lys Val Leu Glu Thr Leu Leu Arg Ser Ser
            420             425             430

Asn Ser Ala Gly Ser Ser His His His His His
            435             440
```

```
<210> SEQ ID NO 22
<211> LENGTH: 311
<212> TYPE: PRT
<213> ORGANISM: Artificial Sequence
<220> FEATURE:
<223> OTHER INFORMATION: Drive de CPH de Neonothopanus nambi
<220> FEATURE:
<221> NAME/KEY: His-tag
<222> LOCATION: (303)..(311)
```

```
<400> SEQUENCE: 22

Met Arg Ile Asn Pro Thr Thr Ser Gly Ser Gly Val Ser Thr Ala Pro
1               5                   10                  15

Ile Ser Ser Thr Trp Ser Arg Leu Ile Arg Phe Val Ala Ile Glu Thr
                20                  25                  30

Ser Leu Val His Ile Gly Glu Pro Ile Asp Ala Thr Met Asp Val Gly
            35                  40                  45

Leu Ala Arg Arg Glu Gly Lys Thr Ile Gln Ala Tyr Glu Ile Ile Gly
        50                  55                  60

Ser Gly Ser Ala Leu Asp Leu Ser Ala Gln Val Ser Lys Asn Val Leu
65                  70                  75                  80

Thr Val Arg Glu Leu Leu Met Pro Leu Ser Arg Glu Glu Ile Lys Thr
                85                  90                  95

Val Arg Cys Leu Gly Leu Asn Tyr Pro Val His Ala Thr Glu Ala Asn
            100                 105                 110

Val Ala Val Pro Lys Phe Pro Asn Leu Phe Tyr Lys Pro Val Thr Ser
        115                 120                 125

Leu Ile Gly Pro Asp Gly Leu Ile Thr Ile Pro Ser Val Val Gln Pro
    130                 135                 140

Pro Lys Glu His Gln Ser Asp Tyr Glu Ala Glu Leu Val Ile Val Ile
145                 150                 155                 160

Gly Lys Ala Ala Lys Asn Val Ser Glu Asp Glu Ala Leu Asp Tyr Val
                165                 170                 175

Leu Gly Tyr Thr Ala Ala Asn Asp Ile Ser Phe Arg Lys His Gln Leu
            180                 185                 190

Ala Val Ser Gln Trp Ser Phe Ser Lys Gly Phe Gly Ser Leu Leu Leu
        195                 200                 205

Thr Ile Arg Met Ala Gln Thr His Ser Gly Asn Ile Asn Arg Phe Ser
    210                 215                 220

Arg Asp Gln Ile Phe Asn Val Lys Lys Thr Ile Ser Phe Leu Ser Gln
225                 230                 235                 240

Gly Thr Thr Leu Glu Pro Gly Ser Ile Ile Leu Thr Gly Thr Pro Asp
                245                 250                 255

Gly Val Gly Phe Val Arg Asn Pro Pro Leu Tyr Leu Lys Asp Gly Asp
            260                 265                 270

Glu Val Met Thr Trp Ile Gly Ser Gly Ile Gly Thr Leu Ala Asn Thr
        275                 280                 285

Val Gln Glu Glu Lys Thr Cys Phe Ala Ser Gly Gly His Glu Gly Ser
    290                 295                 300

Ser His His His His His His
305                 310

<210> SEQ ID NO 23
<211> LENGTH: 1700
<212> TYPE: PRT
<213> ORGANISM: Artificial Sequence
<220> FEATURE:
<223> OTHER INFORMATION: Drive de HispS de Neonothopanus nambi
<220> FEATURE:
<221> NAME/KEY: His-tag
<222> LOCATION: (1692)..(1700)

<400> SEQUENCE: 23

Met Ser Pro Gln Thr Glu Thr Lys Ala Ser Val Gly Phe Lys Asn Ser
1               5                   10                  15

Ser Lys Asn Pro Pro Ser Thr Leu Leu Asp Val Phe Leu Asp Thr Ala
```

-continued

```
              20                    25                    30

Arg Asn Leu Asp Thr Ala Leu Arg Asn Val Leu Glu Cys Gly Glu His
        35                    40                    45

Arg Trp Ser Tyr Arg Glu Leu Asp Thr Val Ser Ser Ala Leu Ala Gln
        50                    55                    60

His Leu Arg Tyr Thr Val Gly Leu Ser Pro Thr Val Ala Val Ile Ser
65                    70                    75                    80

Glu Asn His Pro Tyr Ile Leu Ala Leu Met Leu Ala Val Trp Lys Leu
                  85                    90                    95

Gly Gly Thr Phe Ala Pro Ile Asp Val His Ser Pro Ala Glu Leu Val
                  100                   105                   110

Ala Gly Met Leu Asn Ile Val Ser Pro Ser Cys Leu Val Ile Pro Ser
              115                   120                   125

Ser Asp Val Thr Asn Gln Thr Leu Ala Cys Asp Leu Asn Ile Pro Val
              130                   135                   140

Val Ala Phe His Pro His Gln Ser Thr Ile Pro Glu Leu Asn Lys Lys
145                   150                   155                   160

Tyr Leu Thr Asp Ser Gln Ile Ser Pro Asp Leu Pro Phe Ser Asp Pro
                  165                   170                   175

Asn Arg Pro Ala Leu Tyr Leu Phe Thr Ser Ser Ala Thr Ser Arg Ser
                  180                   185                   190

Asn Leu Lys Cys Val Pro Leu Thr His Thr Phe Ile Leu Arg Asn Ser
              195                   200                   205

Leu Ser Lys Arg Ala Trp Cys Lys Arg Met Arg Pro Glu Thr Asp Phe
        210                   215                   220

Asp Gly Ile Arg Val Leu Gly Trp Ala Pro Trp Ser His Val Leu Ala
225                   230                   235                   240

His Met Gln Asp Ile Gly Pro Leu Thr Leu Leu Asn Ala Gly Cys Tyr
                  245                   250                   255

Val Phe Ala Thr Thr Pro Ser Thr Tyr Pro Thr Glu Leu Lys Asp Asp
                  260                   265                   270

Arg Asp Leu Ile Ser Cys Ala Ala Asn Ala Ile Met Tyr Lys Gly Val
              275                   280                   285

Lys Ser Phe Ala Cys Leu Pro Phe Val Leu Gly Gly Leu Lys Ala Leu
        290                   295                   300

Cys Glu Ser Glu Pro Ser Val Lys Ala His Leu Gln Val Glu Glu Arg
305                   310                   315                   320

Ala Gln Leu Leu Lys Ser Leu Gln His Met Glu Ile Leu Glu Cys Gly
                  325                   330                   335

Gly Ala Met Leu Glu Ala Ser Val Ala Ser Trp Ala Ile Glu Asn Cys
              340                   345                   350

Ile Pro Ile Ser Ile Gly Ile Gly Met Thr Glu Thr Gly Gly Ala Leu
              355                   360                   365

Phe Ala Gly Pro Val Gln Ala Ile Lys Thr Gly Phe Ser Ser Glu Asp
        370                   375                   380

Lys Phe Ile Glu Asp Ala Thr Tyr Leu Leu Val Lys Asp Asp His Glu
385                   390                   395                   400

Ser His Ala Glu Glu Asp Ile Asn Glu Gly Glu Leu Val Val Lys Ser
                  405                   410                   415

Lys Met Leu Pro Arg Gly Tyr Leu Gly Tyr Ser Asp Pro Ser Phe Ser
              420                   425                   430

Val Asp Asp Ala Gly Trp Val Thr Phe Arg Thr Gly Asp Arg Tyr Ser
              435                   440                   445
```

```
Val Thr Pro Asp Gly Lys Phe Ser Trp Leu Gly Arg Asn Thr Asp Phe
    450                 455                 460

Ile Gln Met Thr Ser Gly Glu Thr Leu Asp Pro Arg Pro Ile Glu Ser
465                 470                 475                 480

Ser Leu Cys Glu Ser Ser Leu Ile Ser Arg Ala Cys Val Ile Gly Asp
                485                 490                 495

Lys Phe Leu Asn Gly Pro Ala Ala Ala Val Cys Ala Ile Ile Glu Leu
                500                 505                 510

Glu Pro Thr Ala Val Glu Lys Gly Gln Ala His Ser Arg Glu Ile Ala
                515                 520                 525

Arg Val Phe Ala Pro Ile Asn Arg Asp Leu Pro Pro Pro Leu Arg Ile
    530                 535                 540

Ala Trp Ser His Val Leu Val Leu Gln Pro Ser Glu Lys Ile Pro Met
545                 550                 555                 560

Thr Lys Lys Gly Thr Ile Phe Arg Lys Lys Ile Glu Gln Val Phe Gly
                565                 570                 575

Ser Ala Leu Gly Gly Ser Ser Gly Asp Asn Ser Gln Ala Thr Ala Asp
                580                 585                 590

Ala Gly Val Val Arg Arg Asp Glu Leu Ser Asn Thr Val Lys His Ile
                595                 600                 605

Ile Ser Arg Val Leu Gly Val Ser Asp Asp Glu Leu Leu Trp Thr Leu
    610                 615                 620

Ser Phe Ala Glu Leu Gly Met Thr Ser Ala Leu Ala Thr Arg Ile Ala
625                 630                 635                 640

Asn Glu Leu Asn Glu Val Leu Val Gly Val Asn Leu Pro Ile Asn Ala
                645                 650                 655

Cys Tyr Ile His Val Asp Leu Pro Ser Leu Ser Asn Ala Val Tyr Ala
                660                 665                 670

Lys Leu Ala His Leu Lys Leu Pro Asp Arg Thr Pro Glu Pro Arg Gln
                675                 680                 685

Ala Pro Val Glu Asn Ser Gly Gly Lys Glu Ile Val Val Val Gly Gln
    690                 695                 700

Ala Phe Arg Leu Pro Gly Ser Ile Asn Asp Val Ala Ser Leu Arg Asp
705                 710                 715                 720

Ala Phe Leu Ala Arg Gln Ala Ser Ser Ile Ile Thr Glu Ile Pro Ser
                725                 730                 735

Asp Arg Trp Asp His Ala Ser Phe Tyr Pro Lys Asp Ile Arg Phe Asn
                740                 745                 750

Lys Ala Gly Leu Val Asp Ile Ala Asn Tyr Asp His Ser Phe Phe Gly
                755                 760                 765

Leu Thr Ala Thr Glu Ala Leu Tyr Leu Ser Pro Thr Met Arg Leu Ala
                770                 775                 780

Leu Glu Val Ser Phe Glu Ala Leu Glu Asn Ala Asn Ile Pro Val Ser
785                 790                 795                 800

Gln Leu Lys Gly Ser Gln Thr Ala Val Tyr Val Ala Thr Thr Asp Asp
                805                 810                 815

Gly Phe Glu Thr Leu Leu Asn Ala Glu Ala Gly Tyr Asp Ala Tyr Thr
                820                 825                 830

Arg Phe Tyr Gly Thr Gly Arg Ala Ala Ser Thr Ala Ser Gly Arg Ile
                835                 840                 845

Ser Cys Leu Leu Asp Val His Gly Pro Ser Ile Thr Val Asp Thr Ala
    850                 855                 860
```

-continued

```
Cys Ser Gly Gly Ala Val Cys Ile Asp Gln Ala Ile Asp Tyr Leu Gln
865             870             875             880

Ser Ser Ser Ala Ala Asp Thr Ala Ile Ile Cys Ala Ser Asn Thr His
            885             890             895

Cys Trp Pro Gly Ser Phe Arg Phe Leu Ser Ala Gln Gly Met Val Ser
        900             905             910

Pro Gly Gly Arg Cys Ala Thr Phe Thr Thr Asp Ala Asp Gly Tyr Val
        915             920             925

Pro Ser Glu Gly Ala Val Ala Phe Ile Leu Lys Thr Arg Glu Ala Ala
    930             935             940

Met Arg Asp Lys Asp Thr Ile Leu Ala Thr Ile Lys Ala Thr Gln Ile
945             950             955             960

Ser His Asn Gly Arg Ser Gln Gly Leu Val Ala Pro Asn Val Asn Ser
            965             970             975

Gln Ala Asp Leu His Arg Ser Leu Leu Gln Lys Ala Gly Leu Ser Pro
            980             985             990

Ala Asp Ile Arg Phe Ile Glu Ala  His Gly Thr Gly Thr  Ser Leu Gly
        995             1000                1005

Asp Leu  Ser Glu Ile Gln Ala  Ile Asn Asp Ala Tyr  Thr Ser Ser
    1010            1015            1020

Gln Pro  Arg Thr Thr Gly Pro  Leu Ile Val Ser Ala  Ser Lys Thr
    1025            1030            1035

Val Ile  Gly His Thr Glu Pro  Ala Gly Pro Leu Val  Gly Met Leu
    1040            1045            1050

Ser Val  Leu Asn Ser Phe Lys  Glu Gly Ala Val Pro  Gly Leu Ala
    1055            1060            1065

His Leu  Thr Ala Asp Asn Leu  Asn Pro Ser Leu Asp  Cys Ser Ser
    1070            1075            1080

Val Pro  Leu Leu Ile Pro Tyr  Gln Pro Val His Leu  Ala Ala Pro
    1085            1090            1095

Lys Pro  His Arg Ala Ala Val  Arg Ser Tyr Gly Phe  Ser Gly Thr
    1100            1105            1110

Leu Gly  Gly Ile Val Leu Glu  Ala Pro Asp Glu Glu  Arg Leu Glu
    1115            1120            1125

Glu Glu  Leu Pro Asn Asp Lys  Pro Met Leu Phe Val  Val Ser Ala
    1130            1135            1140

Lys Thr  His Thr Ala Leu Ile  Glu Tyr Leu Gly Arg  Tyr Leu Glu
    1145            1150            1155

Phe Leu  Leu Gln Ala Asn Pro  Gln Asp Phe Cys Asp  Ile Cys Tyr
    1160            1165            1170

Thr Ser  Cys Val Gly Arg Glu  His Tyr Arg Tyr Arg  Tyr Ala Cys
    1175            1180            1185

Val Ala  Asn Asp Met Glu Asp  Leu Ile Gly Gln Leu  Gln Lys Arg
    1190            1195            1200

Leu Gly  Ser Lys Val Pro Pro  Lys Pro Ser Tyr Lys  Arg Gly Ala
    1205            1210            1215

Leu Ala  Phe Ala Phe Ser Gly  Gln Gly Thr Gln Phe  Arg Gly Met
    1220            1225            1230

Ala Thr  Glu Leu Ala Lys Ala  Tyr Ser Gly Phe Arg  Lys Ile Val
    1235            1240            1245

Ser Asp  Leu Ala Lys Arg Ala  Ser Glu Leu Ser Gly  His Ala Ile
    1250            1255            1260

Asp Arg  Phe Leu Leu Ala Tyr  Asp Ile Gly Ala Glu  Asn Val Ala
```

```
    1265               1270               1275

Pro Asp Ser Glu Ala Asp Gln  Ile Cys Ile Phe Val  Tyr Gln Cys
    1280               1285               1290

Ser Val Leu Arg Trp Leu Gln  Thr Met Gly Ile Arg  Pro Ser Ala
    1295               1300               1305

Val Ile Gly His Ser Leu Gly  Glu Ile Ser Ala Ser  Val Ala Ala
    1310               1315               1320

Gly Ala Leu Ser Leu Asp Ser  Ala Leu Asp Leu Val  Ile Ser Arg
    1325               1330               1335

Ala Arg Leu Leu Arg Ser Ser  Ala Ser Ala Pro Ala  Gly Met Ala
    1340               1345               1350

Ala Met Ser Ala Ser Gln Asp  Glu Val Val Glu Leu  Ile Gly Lys
    1355               1360               1365

Leu Asp Leu Asp Lys Ala Asn  Ser Leu Ser Val Ser  Val Ile Asn
    1370               1375               1380

Gly Pro Gln Asn Thr Val Val  Ser Gly Ser Ser Ala  Ala Ile Glu
    1385               1390               1395

Ser Ile Val Ala Leu Ala Lys  Gly Arg Lys Ile Lys  Ala Ser Ala
    1400               1405               1410

Leu Asn Ile Asn Gln Ala Phe  His Ser Pro Tyr Val  Asp Ser Ala
    1415               1420               1425

Val Pro Gly Leu Arg Ala Trp  Ser Glu Lys His Ile  Ser Ser Ala
    1430               1435               1440

Arg Pro Leu Gln Ile Pro Leu  Tyr Ser Thr Leu Leu  Gly Ala Gln
    1445               1450               1455

Ile Ser Glu Gly Glu Met Leu  Asn Pro Asp His Trp  Val Asp His
    1460               1465               1470

Ala Arg Lys Pro Val Gln Phe  Ala Gln Ala Ala Thr  Thr Met Lys
    1475               1480               1485

Glu Ser Phe Thr Gly Val Ile  Ile Asp Ile Gly Pro  Gln Val Val
    1490               1495               1500

Ala Trp Ser Leu Leu Leu Ser  Asn Gly Leu Thr Ser  Val Thr Ala
    1505               1510               1515

Leu Ala Ala Lys Arg Gly Arg  Ser Gln Gln Val Ala  Phe Leu Ser
    1520               1525               1530

Ala Leu Ala Asp Leu Tyr Gln  Asp Tyr Gly Val Val  Pro Asp Phe
    1535               1540               1545

Val Gly Leu Tyr Ala Gln Gln  Glu Asp Ala Ser Arg  Leu Lys Lys
    1550               1555               1560

Thr Asp Ile Leu Thr Tyr Pro  Phe Gln Arg Gly Glu  Glu Thr Leu
    1565               1570               1575

Ser Ser Gly Ser Ser Thr Pro  Thr Leu Glu Asn Thr  Asp Leu Asp
    1580               1585               1590

Ser Gly Lys Glu Leu Leu Met  Gly Pro Thr Arg Gly  Leu Leu Arg
    1595               1600               1605

Ala Asp Asp Leu Arg Asp Ser  Ile Val Ser Ser Val  Lys Asp Val
    1610               1615               1620

Leu Glu Leu Lys Ser Asn Glu  Asp Leu Asp Leu Ser  Glu Ser Leu
    1625               1630               1635

Asn Ala Leu Gly Met Asp Ser  Ile Met Phe Ala Gln  Leu Arg Lys
    1640               1645               1650

Arg Ile Gly Glu Gly Leu Gly  Leu Asn Val Pro Met  Val Phe Leu
    1655               1660               1665
```

```
Ser Asp  Ala Phe Ser Ile Gly  Glu Met Val Ser Asn  Leu Val Glu
    1670             1675              1680

Gln Ala  Glu Ala Ser Glu Asp  Asn Gly Ser Ser His  His His His
    1685             1690              1695

His His
    1700

<210> SEQ ID NO 24
<211> LENGTH: 366
<212> TYPE: PRT
<213> ORGANISM: Artificial Sequence
<220> FEATURE:
<223> OTHER INFORMATION: Drive de NpgA de Aspergillus nidulans
<220> FEATURE:
<221> NAME/KEY: His-tag
<222> LOCATION: (358)..(366)

<400> SEQUENCE: 24

Met Ser Pro Gln Thr Glu Thr Lys Ala Ser Val Gly Phe Lys Val Gln
1               5                   10                  15

Asp Thr Ser Ser Ala Ser Thr Ser Pro Ile Leu Thr Arg Trp Tyr Ile
            20                  25                  30

Asp Thr Arg Pro Leu Thr Ala Ser Thr Ala Ala Leu Pro Leu Leu Glu
        35                  40                  45

Thr Leu Gln Pro Ala Asp Gln Ile Ser Val Gln Lys Tyr Tyr His Leu
    50                  55                  60

Lys Asp Lys His Met Ser Leu Ala Ser Asn Leu Leu Lys Tyr Leu Phe
65                  70                  75                  80

Val His Arg Asn Cys Arg Ile Pro Trp Ser Ser Ile Val Ile Ser Arg
                85                  90                  95

Thr Pro Asp Pro His Arg Arg Pro Cys Tyr Ile Pro Pro Ser Gly Ser
            100                 105                 110

Gln Glu Asp Ser Phe Lys Asp Gly Tyr Thr Gly Ile Asn Val Glu Phe
        115                 120                 125

Asn Val Ser His Gln Ala Ser Met Val Ala Ile Ala Gly Thr Ala Phe
    130                 135                 140

Thr Pro Asn Ser Gly Gly Asp Ser Lys Leu Lys Pro Glu Val Gly Ile
145                 150                 155                 160

Asp Ile Thr Cys Val Asn Glu Arg Gln Gly Arg Asn Gly Glu Glu Arg
                165                 170                 175

Ser Leu Glu Ser Leu Arg Gln Tyr Ile Asp Ile Phe Ser Glu Val Phe
            180                 185                 190

Ser Thr Ala Glu Met Ala Asn Ile Arg Arg Leu Asp Gly Val Ser Ser
        195                 200                 205

Ser Ser Leu Ser Ala Asp Arg Leu Val Asp Tyr Gly Tyr Arg Leu Phe
    210                 215                 220

Tyr Thr Tyr Trp Ala Leu Lys Glu Ala Tyr Ile Lys Met Thr Gly Glu
225                 230                 235                 240

Ala Leu Leu Ala Pro Trp Leu Arg Glu Leu Glu Phe Ser Asn Val Val
                245                 250                 255

Ala Pro Ala Ala Val Ala Glu Ser Gly Asp Ser Ala Gly Asp Phe Gly
            260                 265                 270

Glu Pro Tyr Thr Gly Val Arg Thr Thr Leu Tyr Lys Asn Leu Val Glu
        275                 280                 285

Asp Val Arg Ile Glu Val Ala Ala Leu Gly Gly Asp Tyr Leu Phe Ala
    290                 295                 300
```

-continued

```
Thr Ala Ala Arg Gly Gly Gly Ile Gly Ala Ser Ser Arg Pro Gly Gly
305             310             315             320

Gly Pro Asp Gly Ser Gly Ile Arg Ser Gln Asp Pro Trp Arg Pro Phe
                325             330             335

Lys Lys Leu Asp Ile Glu Arg Asp Ile Gln Pro Cys Ala Thr Gly Val
            340             345             350

Cys Asn Cys Leu Ser Gly Ser Ser His His His His His His
        355             360             365
```